US012653561B2

(12) United States Patent
Heimberger

(10) Patent No.: US 12,653,561 B2
(45) Date of Patent: Jun. 16, 2026

(54) ENDOSCOPIC INSTRUMENT FOR INSERTING INTO A BODY OF A PATIENT

(71) Applicant: Richard Wolf GmbH, Knittlingen (DE)

(72) Inventor: Rudolf Heimberger, Oberderdingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 1441 days.

(21) Appl. No.: 17/291,778

(22) PCT Filed: Nov. 7, 2019

(86) PCT No.: PCT/DE2019/200125
§ 371 (c)(1),
(2) Date: May 6, 2021

(87) PCT Pub. No.: WO2020/094188
PCT Pub. Date: May 14, 2020

(65) Prior Publication Data
US 2021/0386441 A1    Dec. 16, 2021

(30) Foreign Application Priority Data
Nov. 7, 2018    (DE) ..................... 10 2018 218 954.4

(51) Int. Cl.
*A61B 17/221* (2006.01)
*A61B 1/00* (2006.01)
(Continued)

(52) U.S. Cl.
CPC ........ *A61B 17/221* (2013.01); *A61B 1/00066* (2013.01); *A61B 1/00078* (2013.01);
(Continued)

(58) Field of Classification Search
CPC ..... A61B 1/015; A61B 1/0057; A61B 17/211; A61B 17/00234; A61B 17/22078;
(Continued)

(56) References Cited

U.S. PATENT DOCUMENTS

2002/0198551 A1* 12/2002 Grant ....................... A61B 1/12
606/159
2006/0020165 A1* 1/2006 Adams ............... A61B 1/00142
600/157
(Continued)

FOREIGN PATENT DOCUMENTS

EP          2986237 B1     3/2018
GB          2268883 A   *  1/1994 ............. A61B 1/015

*Primary Examiner* — John P Leubecker
*Assistant Examiner* — Li-Ting Song
(74) *Attorney, Agent, or Firm* — McGlew and Tuttle, P.C.

(57) ABSTRACT

An endoscopic instrument (1, 134) for inserting into a body of a patient includes a tubular shank (3, 47, 137) and at least two electrical, mechanical and/or optical leads (11, 13, 15, 19, 57, 59, 65, 67, 123, 181) which run through the shank (3, 47, 137). A fluid channel (7, 53) is formed in the shank (3, 47, 137). The instrument includes a sealing device (89) which forms a proximal end of the fluid channel and comprises feed-throughs (93, 97, 99, 101, 103) for the leads (11, 13, 15, 19, 57, 59, 65, 67, 123, 181).

35 Claims, 9 Drawing Sheets

(51) Int. Cl.

| | |
|---|---|
| *A61B 1/005* | (2006.01) |
| *A61B 1/015* | (2006.01) |
| *A61B 1/018* | (2006.01) |
| *A61B 1/07* | (2006.01) |
| *A61B 17/00* | (2006.01) |
| *A61B 17/22* | (2006.01) |

(52) U.S. Cl.
CPC ...... *A61B 1/00103* (2013.01); *A61B 1/00114* (2013.01); *A61B 1/00117* (2013.01); *A61B 1/00119* (2013.01); *A61B 1/0052* (2013.01); *A61B 1/0055* (2013.01); *A61B 1/015* (2013.01); *A61B 1/018* (2013.01); *A61B 1/07* (2013.01); *A61B 17/00234* (2013.01); *A61B 2017/0023* (2013.01); *A61B 2017/00238* (2013.01); *A61B 2017/00296* (2013.01); *A61B 2017/0046* (2013.01); *A61B 2017/22078* (2013.01); *A61B 2017/2212* (2013.01)

(58) Field of Classification Search
CPC ........ A61B 17/2212; A61B 2017/0023; A61B 2017/00238; A61B 2017/00296; A61B 2017/0046; A61B 2017/22078; A61B 2017/2212; A61B 1/00137; A61B 1/018; A61B 2017/2948; A61B 2017/3466

See application file for complete search history.

(56) References Cited

U.S. PATENT DOCUMENTS

| | | | | |
|---|---|---|---|---|
| 2008/0091074 A1* | 4/2008 | Kumar | ................... | A61B 1/012 |
| | | | | 600/156 |
| 2010/0087705 A1 | 4/2010 | Byers et al. | | |
| 2012/0010464 A1* | 1/2012 | Adams | ................... | A61B 1/303 |
| | | | | 600/156 |
| 2014/0221749 A1 | 8/2014 | Grant et al. | | |
| 2016/0096004 A1 | 4/2016 | Gerrans et al. | | |
| 2016/0174819 A1* | 6/2016 | Ouyang | ............ | A61B 1/00098 |
| | | | | 600/105 |
| 2016/0302997 A1* | 10/2016 | Ledel | ................. | A61B 1/00119 |
| 2017/0188794 A1* | 7/2017 | Ouyang | ............ | A61B 1/00066 |
| 2017/0215965 A1* | 8/2017 | Harrah | ................... | A61B 1/018 |
| 2017/0238793 A1 | 8/2017 | Govrin et al. | | |
| 2018/0125339 A1* | 5/2018 | Gerbo | .................... | A61B 1/005 |
| 2018/0344993 A1* | 12/2018 | Ganz | ..................... | A61B 50/30 |
| 2019/0254504 A1* | 8/2019 | Ide | ........................ | A61B 1/018 |
| 2019/0282071 A1* | 9/2019 | Ouyang | ............ | A61B 1/00052 |
| 2019/0298321 A1* | 10/2019 | Intintoli | .................. | A61B 1/07 |
| 2019/0328217 A1* | 10/2019 | Moreau | ............. | A61B 1/00183 |
| 2020/0196843 A1* | 6/2020 | Tah | ........................ | A61M 1/774 |
| 2021/0085158 A1* | 3/2021 | Ikuma | .............. | A61B 1/00068 |
| 2022/0053998 A1* | 2/2022 | Ghani | ................... | A61B 18/26 |
| 2023/0148841 A1* | 5/2023 | Brecht | .............. | A61B 1/00137 |
| | | | | 600/104 |
| 2023/0165439 A1* | 6/2023 | Govrin | .............. | A61B 1/00091 |
| | | | | 600/431 |
| 2023/0248434 A1* | 8/2023 | Altshuler | ........... | A61B 1/00137 |
| | | | | 600/108 |
| 2024/0252027 A1* | 8/2024 | Sørensen | ........... | A61B 1/00066 |

* cited by examiner

Fig. 4A
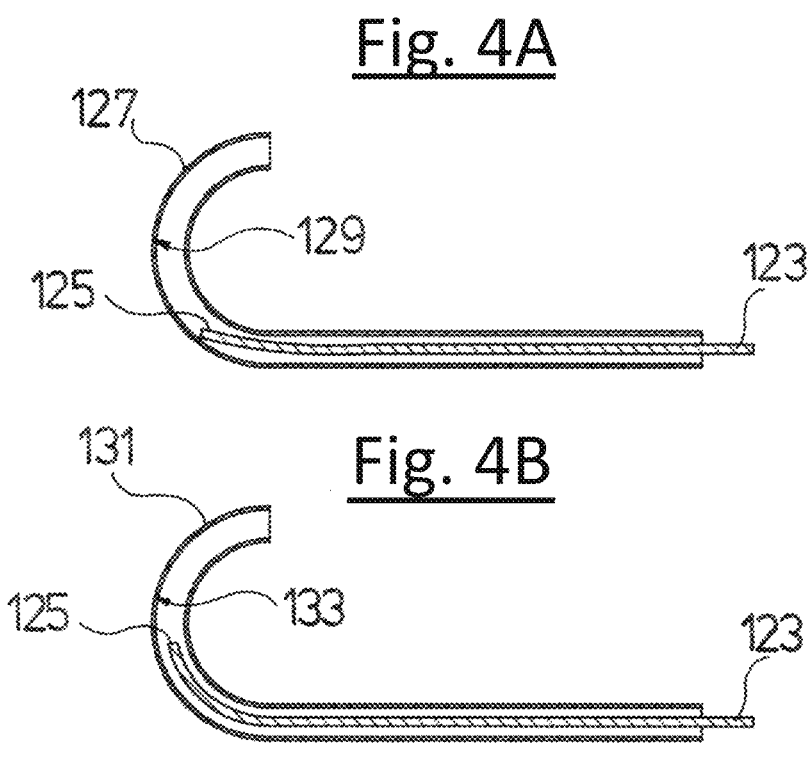
Fig. 4B
Fig. 5
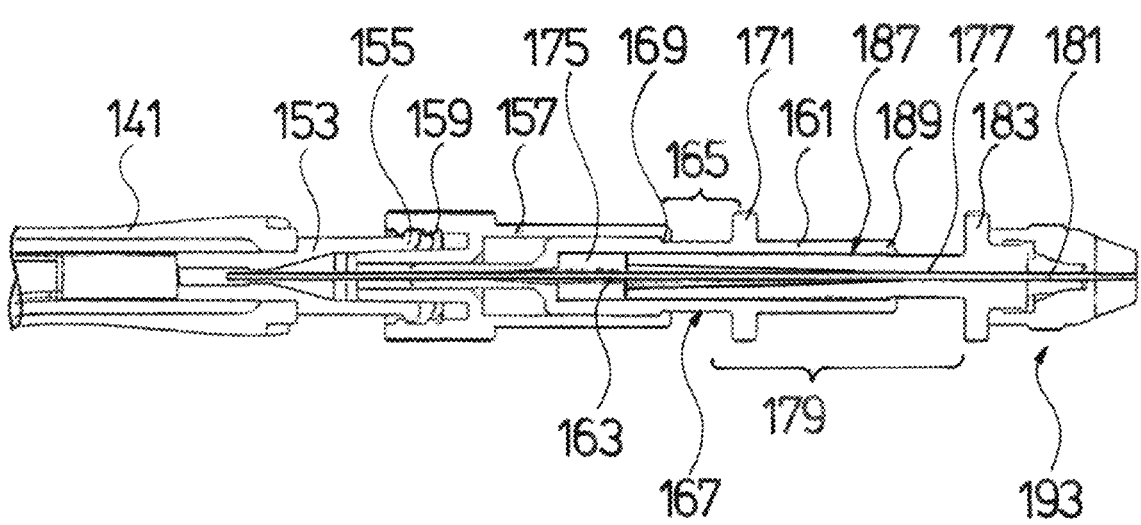

ENDOSCOPIC INSTRUMENT FOR INSERTING INTO A BODY OF A PATIENT

CROSS REFERENCE TO RELATED APPLICATIONS

This application is a United States National Phase Application of International Application PCT/DE2019/200125, filed Nov. 7, 2019, and claims the benefit of priority under 35 U.S.C. § 119 of German Application 10 2018 218 954.4, filed Nov. 7, 2018, the entire contents of which are incorporated herein by reference.

TECHNICAL FIELD

The disclosure relates to an endoscopic instrument for inserting into a body of a patient, preferably as a disposable article for disposal after using once and preferably for the minimal-invasive diagnosis of kidney tubes and ureters as well as for the removal of kidney and urinary stones.

TECHNICAL BACKGROUND

The starting point of the invention are uretero-renoscopes as are known for instance from EP 2 986 237 B1. A shank of the uretero-renoscope is inserted into the body of a patient via the ureter, in order with a distal gripping means such as for instance a capture basket or a Dormia loop, to capture a kidney stone or a urinary stone and to remove it. Such uretero-renoscopes however can not only be used therapeutically, but also merely diagnostically, since the treating person can herewith view and diagnose the kidney tube or ureter in a direct manner. Usually, the visibility is improved by rinsing fluid which at the distal end of the shank exits through a rinsing conduit which is led through the shank, and carries along tissue which inhibits the view.

There is the constant desire to reduce the shank diameter of such instruments, in order to fashion the medical operation in a minimal invasive manner as much as possible or to better utilize the cross section which is available, in order to be able to provide more or improved functionalities given the same cross section.

SUMMARY

The endoscopic instrument which is disclosed herein can be configured with a smaller shank diameter than known endoscopic instruments of this type or utilizes the cross section which is available to a better extent, in order given the same cross section to be able to provide more or improved functionalities.

According to an aspect of the present disclosure, an endoscopic instrument for inserting into a body of a patent is provided, wherein the instrument comprises a tubular shank and at least two electrical, mechanical and/or optical leads which run through the shank. The instrument can herein comprise a fluid channel and a sealing means (sealing device) which forms a proximal end of the fluid channel and comprises feed-throughs for the leads. The seal device can comprise for example an elastomer cell foam block which is arranged in a proximal end region of the shank and/or in a handling device which is connected or connectable to a proximal end region of the shank. Preferably, the cell foam block is configured in a closed-celled manner. The leads can be led through the seal device through feed-throughs, wherein the feed-throughs each have an initially smaller diameter than the associated, led-through lead, however are elastically widened by the led-through lead. By way of this, a sealing effect can be achieved, so that no fluid can flow proximally through the feed-throughs axially out of the shank to the outside or into the handling device. The fluid specifically is preferably not to flow axially, but laterally through a proximal fluid channel opening which is provided for this and which is arranged laterally on the shank and preferably distally of the seal device.

According to the present disclosure, on use of an endoscopic instrument which comprises a shank which can be coupled to a handling device and is with a jointlessly bendable distal tip and in which a fluid channel is formed, a seal device or a sealing means is provided, in order to seal the leads with respect to the handling device. As a result, the sealing means forms a proximal end of the fluid channel. The sealing means is preferably coupled to the shank in a rotationally fixed manner. The rotating of the shank consequently leads to a rotating of the leads and of the sealing means, so that the relative positions of the leads which are led through the sealing means, to the sealing means, remain unchanged. The sealing means is therefore not loaded by transverse forces which could elastically deform the material of the sealing means to such an extent that a sealing effect is at least regionally lifted. The rotationally fixed coupling can be realized by way of positive-fit means which are formed in the sealing means and in the seal receiver in a manner corresponding to one another.

Optionally, the sealing means has a disc-like, round shape. Herein, the sealing means can be easily pressed into the seal receiver.

Optionally, the positive-fit means can be realized in the form of a peripheral tongue and groove arrangement. The groove can project into a peripheral surface of the sealing means or be formed in the seal receiver. The tongue could be formed in the seal receiver or in the sealing means as a radial projection. The positive fit means are preferably arranged exclusively at a single, peripheral-side position, so that a correct placement of the sealing means is achieved even in the case of a sealing means which is configured in a non-symmetrical manner.

Optionally, the sealing means can comprise at least two slots as feed-throughs which pass through a peripheral surface of the sealing means and each extend partly through the sealing means. The slots can be provided for leading mechanical leads such as for instance pull wires, through the sealing means. The pull wires extend from the handling device to the distal end of the shank and can be used to jointlessly bend the distal tip. If the pull wires are configured as flat wires, then these can also be sealingly led through the sealing means in a reliable manner.

Optionally, the sealing means can comprise four slots as feed-throughs, said slots being arranged in the sealing means in a manner distanced to one another. As a result, the sealing means can also be applied for sealing a fluid channel in a shank of an endoscopic instrument, concerning which the tip is jointlessly bendable in a main bending plane and additionally moveable in a second bending plane. Consequently, the endoscopic instrument can comprise four mechanical leads in the form of pull wires or the like, which are led through the four slots and extend through the shank. The size and alignment of the slots is herein dependent on the type and arrangement of the pull wires.

Further optionally, the slots can also be based on radial lines which are displaced in parallel and which are offset to one another by at least 90° on a surface which is covered by the sealing means. The slots can project beyond a middle line which runs perpendicularly to the respective slot and which intersects a middle point of the sealing means. If four pull wires are applied, then four slots are necessary and these are then offset to one another for example by 90°. Given only two pull wires, two slots can be sufficient and these are then offset to one another for example by 180°.

Optionally, the sealing means can be manufactured of a material which comprises polyethylene or cellular rubber. Cellular rubber can be based for example on a fluoropolymer.

Optionally, the endoscopic instrument which comprises the sealing means explained above can comprise a shank connection part which is rotatable in a control housing and which is fixedly connectable to the shank. The shank connection part can optionally comprise a connection pipe stub which extends radially outwards from a shank connection axis. Optionally, a sealing ring can be arranged between a seal receiver for receiving the sealing means and the shank connection part, in order to achieve a sealing.

Further optionally, the shank connection part comprises guide devices for guiding pull wires. By way of guiding the pull wires, these can directly follow each rotation of the shank connection part. A crossing of the pull wires and of the associated slots in the sealing means can be prevented, so that the sealing effect is not compromised by way of this. The seal receiver can further be supplemented by a cover in the distal direction, said cover being away from the shank connection part, wherein the cover is likewise coupled to the shank connection part in a rotationally fixed manner. The cover can further likewise comprise guide devices, with which pull wires can be led. The guide devices in the cover and in the shank connection part are preferably flush, so that the sealing means experiences exclusively axial forces of the pull wires.

Optionally, the fluid channel can individually directly surround the at least two leads which run through the shank. Here "individually directly surrounds" is to mean that the leads have no common sheathing within the fluid channel, but can be peripherally rinsed by fluid in the fluid channel in a direct manner. The leads can each be sheathed individually and for example be insulated. "Directly" here is therefore not to be misunderstood to the extent that the leads may not have a sheathing themselves. The leads can be of an optical nature, for example as fiber optics for coupling in and coupling out light at the distal end. In particular, the leads can comprise one or more laser fiber optics, in order for example to shoot a kidney or urinary stone with laser light and to thus valorize it. Alternatively or additionally, one or more of the leads can transmit electrical signals and/or electrical power and be connected to a distal LED and/or to a distal picture sensor. Alternatively or additionally, the leads can comprise one or more working channels, through which shank tools and/or a laser fiber optic can be pushed up to the distal shank tip. Alternatively or additionally, the leads can transmit mechanical control signals for bending and/or controlling the distal shank end, for example as pull cables which are led laterally in the shank. All leads are each individually directly surrounded by the fluid channel. "Surrounded" here is to mean that the leads at least to the larger part are peripherally rinsed in cross section. They do not need to be completely peripherally rinsed in cross section by 360°, but can bear laterally on the shank or on one or more of the other leads.

On the one hand, concerning the endoscopic instrument which is disclosed here, a fluid lead which is led through the shank can be done away with. Furthermore, the complete cross section of the inner volume of the shank which the leads do not occupy can be used as a fluid channel, so that the available cross section is better utilized. Herein, a shank outer diameter of 3 mm or less can be realized.

Optionally, the fluid channel can serve as a feed channel and/or discharge channel. Depending on the requirement, rinsing fluid for improving the view at the distal shank end can be fed distally or rinsing fluid with an annoying tissue suspension can be led away proximally. A return of fluid proximally can be effected by way of active suctioning or passively without active suctioning, for example by way of overpressure in the body of the patient.

Optionally, the fluid channel can comprise a distal fluid channel opening and a proximal fluid channel opening, wherein the proximal fluid channel opening is arranged laterally on the shank and can be subjected to fluid pressure or fluid vacuum. For this, a pressure pump or vacuum pump can be connected onto the proximal fluid channel opening or a fluid reservoir which is located at a height above the instrument can be connected, as with a drip, so that a hydrostatic pressure bears in the proximal fluid channel opening. A saline solution can serve for example as a rinsing fluid.

Optionally, the instrument can comprise a handling device which is fixedly connected or releasably connectable to a proximal end of the shank. The handling device can preferably be configured ergonomically, such that it can be comfortably gripped by a treating person and lies well in the hand, in order to manually control the instrument. For this, the handing device can be configured in an essentially Y-shaped manner with two rigid grip limbs which distally run together towards the shank. The handling device can either be gripped such that both grip limbs can be gripped around as a forceps or the ball of the thumb is led between the grip limbs. Concerning the first posture, the index finger can be applied on a gun-like trigger for pulling a pull cable below the shank. Concerning the second posture, the index finger can be applied on an upper trigger for pulling an upper pull cable above the shank and the middle finger applied on a lower trigger for pulling a lower pull cable below the shank. The upper pull cable and the lower pull cable can be configured as sections of a pull cable which is deflected around a guide roller which in the handling device is rotatably mounted about an axis which is transverse to the longitudinal axis of the shank. Depending on the rotation direction of the guide roller, the upper or the lower pull cable is pulled proximally whilst the respective other pull cable yields distally. The upper trigger and the lower trigger can each be directly connected to one another via a guide roller or be coupled in an indirect manner, so that they move oppositely on actuation. It is particular the second posture is ergonomically particularly advantageous, since the longitudinal axis of the shank runs essentially coaxially to the longitudinal axis of the lower arm, so that the instrument can be comfortably rotated by supination and pronation of the lower arm about its longitudinal axis. Furthermore, by way of actuating the upper or lower trigger with the index finger or middle finger, an abrupt bending of the distal shank end can be effected in two opposite directions by way of the upper and lower pull cable. Concerning the first posture, the handling device can be peripherally gripped by 180°, in order to pull the other trigger with the index finger, or the instrument can be rotated by 180° about its longitudinal axis, in order to effect an abrupt bending of the distal shank end by way of the upper or lower pull cable in two opposite directions. The leads can be led through one or both of the grip limbs of the handling device and at a proximal end of the grip limb or grip limbs can each comprise a proximal-side connection. A working channel is preferably led through a grip limb of the handling device and other leads through the other grip limb of the handling device.

Optionally, the shank at least in a shank section can be jointlessly elastically bendable by more than 270°. In particular, a high torsional stiffness given a certain bending flexibility is advantageous for the exact control of the distal shank end. The bending stiffness can be quantitatively dimensioned by way of how deep the distal shank end sags downwards solely under the weight force of the shank given a horizontal position of the instrument. It has been found that it is particularly advantageous if the distal shank end solely by the weight force of the shank sags downwards by 5% to 60% of the shank length given a horizontal position of the instrument. In this range of the bending stiffness, the shank is flexible enough, in order to be able to penetrate as deeply and simultaneously minimally invasively as possible into the kidney tube and ureter and is flexurally rigid enough, in order to be able to control the distal shank end in a controlled manner.

Optionally, the instrument or at least the shank can be configured as a disposable article for disposal after having been used once. This is a particularly advantageous embodiment since the cleaning of the instrument for further uses is done away with and the components and materials only need to be configured for a single use. The leads which are individually directly surrounded by the fluid channel can be configured in a very delicate manner and without consideration of the configuration of poorly cleanable corners, edges and/or dead spaces by the fluid channel. On account of the delicate configuration of the leads and the shank itself, a shank outer diameter of 2.7 mm or less can be realized.

Optionally, the cross-sectional area of the fluid channel can correspond to the cross-sectional area of a shank interior which is formed by the shank, minus the sum of the cross-sectional area of all leads which run through the shank interior. This means that no unused cross-sectional area results in the shank and the shank interior can therefore be optimally utilized.

Optionally, the shank can comprise a plurality of slots in a distal region. Herein, the slots can only extend over a part of the shank periphery in the circumferential direction. Herein, the flexibility of the shank can be locally increased, thus the bending radius can be locally reduced, in order to achieve a jointless bending of the distal shank end by up to 300°. Alternatively or additionally, the slots can be arranged axially to one another in a manner such that they lie alternately on a first lateral side of the shank and on a second lateral side of the shank which lies diametrically opposite the first. Herewith, the distal shank end can be jointlessly bent in two opposite directions and given pull cables which are accordingly actuatable independently of one another can even execute two opposite curved bends in an S-shaped manner. For the curved bending to a first side, the slots are pressed together at a first aside and the slots are pulled apart at a second side which is opposite to the first side. Accordingly, for the curvature to the second side, the slots are pressed together at the second side and the slots are pulled apart at the first side. The pull cables then preferably run in the shank along the first and second side and engage on the distal shank end, in order to jointlessly bend away the distal shank end to the respective side by way of a pulling force.

Optionally, the slots on the one hand can serve as a distal fluid channel opening for the fluid channel and on the other hand for locally increasing the flexibility of the shank for the jointless bending away of a distal shank end. The rinsing fluid can then exit laterally out of the shank proximally of the distal shank end. Amongst other things, this has the advantage that more cross section for functions such as for instance a picture sensor and/or at least one illumination LED is available at the distal shank end.

Optionally, the instrument can comprise at least one working channel which runs through the shank and is directly surrounded by the fluid channel. Such a working channel can be selectively used in different manners. On the one hand such a working channel can be suitable for leading through a shank tool, such as for instance a capture basket inert or a forceps instrument. Inasmuch as the instrument does not already comprises an optical lead such as a laser fiber optic which is led through the fluid channel, such a laser fiber optic can be introduced through preferably a further working channel from a proximal working channel opening, for example at a proximal axial end of a grip limb of the handling device, and be pushed through the working channel up to a distal working channel opening at the distal shank end. Laser light can be coupled in by the laser fiber optic, in order for example to valorize a kidney stone or urinary stone and to flush it out of the rinsing channel by way of rinsing fluid. The laser fiber optic when not in use can be withdrawn from the working channel again, in order to release this for possible other uses. For example, a capture basket insert or a Dormia loop insert can be pushed through the working channel, in order herewith to capture a kidney stone or urinary stone at the distal shank end. The proximal working channel opening, for example at a proximal axial end of a grip limb of the handling device can comprise a Luer lock connection, in order to fix a jacket of a capture basket insert or of the Dormia loop insert with respect to the instrument, and by way of pushing a wire which leads through the jacket and which at the distal side forms the capture basket or the Dormia loop, to open the capture basket or the Dormia loop. The capture basket or the Dormia loop closes on pulling the wire when the jacket is arrested in the Luer lock connection. However, it is preferable for a first, preferably larger working channel to be provided for a shank tool and a second, preferably smaller working channel to be provided for a laser fiber optic. The shank tool and the laser fiber optic can be used in parallel by way of this.

Optionally, a working channel can serve as a feed channel and/or discharge channel with a flow direction which is opposite with respect to the fluid channel. In particular, this is advantageous if, given a longer treatment time and larger quantities of rinsing fluid, this must be led away out of the body again without interrupting the treatment. A return of rinsing fluid at the outer side of the shank or through an additionally inserted auxiliary shank leads to an additionally expansion of the tissue and is disadvantageous with respect to a minimal invasive operation. Furthermore, an overpressure can build up, such counteracting the flow of rinsing agent. The working channel can preferably be used as a feed conduit of rinsing fluid which is led away via the fluid channel as a discharge conduit. Alternatively, the flow of rinsing agent can run the other way round, so that the working channel serves as a discharge channel and the fluid channel as a feed channel. The use of the working channel as a feed channel and/or as a discharge channel can simplify a continuous rinsing.

Optionally, the at least one working channel can run axially through the sealing means. The working channel therefore, analogously to the other leads, can be led through an associated axial feed-through in the seal device which is configured for example in the form of an elastomer cell foam block.

Optionally, the proximal working channel opening can be arranged proximally of the proximal end of the fluid channel, preferably at a proximal axial end of a grip limb of the handling device. Herewith, the working channel can be used in a comprehensive as possible manner and is as straight as possible which is to say has only relatively large bending radii.

Optionally, the distal working channel opening can be arranged distally of a distal fluid channel opening of the fluid channel. Herewith, in particular a kidney stone or urinary stone which is smashed can be led away through the working channel, wherein clear viewing conditions are created by way of the lateral discharge or run-off of rinsing fluid through the fluid channel opening.

Optionally, the cross section of the distal working channel opening can be smaller than the cross section of the working channel. Herewith, the risk of blockage of the working channel is reduced, since the smaller working channel opening acts as a filter to large pieces of tissue and these cannot pass through the working channel opening.

Optionally, the cross section of the distal working channel can taper towards the distal working channel opening. Herewith, an inner-side step or edge in front of the smaller working channel opening is avoided, on which a laser fiber optic which is inserted through the working channel, a capture basket insert and/or a Dormia loop insert could snag.

Optionally, a throughflow direction and/or throughflow rate through the fluid channel can be selected or set. This can be carried out for example via a pressure control and/or by way of opening and closing a valve, preferably on the proximal fluid channel opening.

Optionally, a distal shank end can be jointlessly bendable in a controllable manner. This can be preferably realized as described above via a bending flexibility of the shank which is locally increased by way of lateral slots in the shank, and via at least one pull cable which laterally engages on the distal shank end.

According to a further aspect of the present disclosure, on use of a fiber optic and in particular a laser fiber optic with an outer diameter of significantly below 1 mm in a shank of an endoscopic instrument with a jointlessly bendable distal tip, one can apply a dedicated working channel with an inner diameter which is significantly less than the inner diameter of a conventional working channel. It is preferable for the inner diameter of the working channel for a fiber optic to exceed the outer diameter of a fiber optic by 30% at the most. By way of this, one allows a fiber optic to be able to be displaced in the working channel of the endoscopic instrument even in the case of a jointlessly bent distal tip of this. A relatively sharp-edged end of the fiber optic, on account of the specified diameter ratio, undergoes only a relatively small engagement angle to its surface and does not injure it, even in the case of an arcuate course of the working channel. The working channel and the endoscopic instrument are consequently not un-tight and can be used or a further duration. A rinsing performance is further improved by way of replacing a conventional working channel by a significantly narrower working channel. The outer diameter of the fiber optic can lie in a region of 0.4 mm to 0.7 mm, preferably in a region of 0.45 mm to 0.6 mm and particularly preferably of 0.45 to 0.5 mm. It particularly lends itself to equip an endoscopic instrument with such a separate working channel, concerning which a fluid channel which individually directly surrounds two leads which run through the shank is formed in the shank. In particular, it lends itself to insert this separate working channel in a distal region which is applied with slots, in order to yet further optimize the size of the fluid channel which is formed therein. Little space is taken up in the inner volume of the fluid channel due to the low diameter. As mentioned above, the fiber optic can in particular be a laser fiber optic.

Optionally, the material of the separate working channel for the fiber optic can be polyimide or polyamide. The working channel for the fiber optic should consist of a hard as possible material and herein it should change its cross section as little as possible in the bent state. By way of this, the danger of the fiber optic penetrating into the inner surface of the working channel is significantly reduced. The material for the working channel can be for instance poly-imide or polyamide (also known as nylon) in a corresponding hardness.

Optionally, the wall of the separate working channel can comprise reinforcements for the fiber optic. In particular, these can run in circumferential direction and prevent a bending collapse of the cross section of the separate working channel.

Further optionally, the material of the separate working channel can also comprise a metallic material. This can comprise for instance nitinol which is a nickel-titanium alloy with super elastic characteristics at room temperature. This material can have the demanded and necessary elasticity/flexibility/bending possibility given the aforementioned small diameters.

According to a further aspect of the present disclosure, on use of an endoscopic instrument with a shank with a jointlessly bendable distal tip, an arrangement of first slots which are optionally located alternately on a first lateral side of the shank and on a second lateral side of the shank which is diametrically opposite to the first can be provided. By way of this one can achieve a bending in a main bending plane without having to create individual segments which are connected by a joint and which partly extend into the inner lumen of the shank. For further improving the movability, optionally several second slots which are offset to the first slots by 90° can connect proximally onto the region with first slots. The second slots can extend in the circumferential direction preferably only over a part of the shank periphery. Further preferably, the two slots are arranged axially to one another in a manner such that they alternately lie on a third lateral side of the shank and a fourth lateral side of the shank which lies diametrically opposite the third. By way of this, a second bending plane which lies transversely to the main bending plane is formed.

The movablility in the second bending plane can be adjusted depending on the number of second slots. It particularly lends itself to select the number of the second slots in a manner such that the distal end of the shank is bendable in the second bending plane about an angular range of at least +/−15 and preferably of +/−20. It is particularly the ability to reach kidney stones in the lower caliceal region of the kidneys which can be improved by way of this.

The movement of the distal end of the shank in the second bending plane can be achieved by way of separate mechanical leads in particular pull wires. These are coupled to the shank in a direct manner distally in front of the region which is provided with second slots. An aforementioned handling device can be applied for moving the pull wires.

According to a further aspect of the present disclosure, concerning an endoscopic instrument which comprises a shank which can be coupled to a handling device, a shank tool, for example with a capture basket which is integrated therein or a forceps, can be pushed through a working channel of the instrument onto the distal end of the instrument. The handling device for this can preferably comprise a working channel inlet, a first rotatable receiving part and a second receiving part which is connected to the first receiving part in a rotationally fixed manner. The first receiving part can be fixedly coupled to a jacket element of the shank tool, for example via a Luer connection, nonetheless be displaceably mounted for the exact axial positioning relative to the working channel inlet. The second receiving part can be coupled to a distal tool head, for example a capture basket or forceps jaw parts, via a control wire which is led through the jacket element of the shank tool, and be axially displaceably mounted relative to the first receiving part. The shank tool can be pushed in the instrument into different axial positions through the first receiving part. By way of this, it is possible to insert the shank tool through the shank onto the distal shank tip in a positioned manner, so that it firstly does not project beyond it. The distal shank tip can consequently be moved to an operation region in an uninhibited manner and a danger of injury due to a sharp-edged tool head is avoided. After reaching the operational region, by way of displacing the first receiving part in the distal direction, the shank tool can be pushed out of the distal shank end. The wire which is coupled to the tool head, for example the capture basket or forceps jaw parts, as the case may be can then be subsequently pushed out of the jacket element of the shank tool by way of displacing the second receiving part. The shank tool can be rotated by way of a rotationally fixed coupling of the shank tool and of the first receiving part as well as a rotationally fixed coupling between the second receiving part and the first receiving part. By way of such a construction, furthermore it is very easily possible to position and actuate the shank tool by a single user. Coordination with a second user is consequently not necessary.

The first receiving part is optionally displaceable with respect to the working channel inlet by a first displacement path. The second receiving part is movable relative to the first receiving part by a second displacement path. The length of the second displacement path can herein optionally exceed or fall short of the length of the first displacement path. The first displacement path is exclusively conceived to bring the shank tool into a position which lies axially outside the distal shank tip. Herewith, the tool head can be extended out of the distal tip without hindrance. The length of the first displacement path can merely be a few millimeters. It is conceivable to provide a displacement path of roughly 5 mm. The first displacement part can also lie in a range of 2 mm to 10 mm depending on the configuration of the endoscopic shank. The second displacement path in the meanwhile is dependent on the type and size of the tool head and can be for example up to 20 or 25 mm.

The first receiving part and/or the second receiving part can optionally be held in a momentary axial and/or rotated position via latching means. The first receiving part and/or the second receiving part for example could have a lateral surface which is provided with peripheral grooves which are arranged parallel to one another, wherein the grooves each comprise a rounded profile cross section. If these are led through a suitably dimensioned opening, the latching can be effected between two consecutive grooves. The latched position however can also be released again by way of a suitable force transverse to the grooves.

The first receiving part and/or the second receiving part can further be configured with a shoulder which comprises a knurling. By way of this, a user can easily grip the respective receiving part and carry out a rotation by feel and with a direct haptic feedback.

According to a further aspect of the present disclosure, the handling device of an endoscopic instrument which is provided with a shank can comprise a housing which at a proximal end comprises two limbs which are arranged obliquely to one another and enclose a contact surface, wherein at least one lead is led outwards out of the handling device out of one of the limbs. The handling device can consequently be configured at a proximal end as a Y or a V. It is possible for a user to grip the handling device such that a ball of the thumb of a hand bears on the contact surface and two further fingers of the hand, for example the index finger and middle finger can be led to triggers or operating levers which are arranged distally. The housing is configured in a manner such that the ball of the thumb can lie on the contact surface such that the handling device forms a direct extension of the lower arm of the user. A rotating of the lower arm leads to a direct and exclusive rotation of the handling device about the longitudinal axis of the shank, so that the shank which is attached thereto is also rotated about its longitudinal axis by way of this.

Optionally at least one can disc cam follow distally connecting onto the two limbs, said cam disc being connected preferably at the radial side to pull wires and at least two triggers or operating levers for moving the at least one cam disc. The cam disc is preferably rotatable in two directions in an angular range about a rotation axis in the housing of the handling device, wherein the rotation axis preferably runs essentially perpendicularly to a plane which is spanned by the two limbs.

The at least one cam disc is optionally fixable in its momentary position via an arresting device. The arresting device could be realized for example in the form of a knurled screw, with which a user can arrest a position of the at least one cam disc, said position having been set once. A jointless bending which is created by the pull wires can consequently remain in its state, without it having to be retained by way of permanent manual intervention which is demanding.

The previously described aspects of the present disclosure although being preferably applied in an arbitrary combination in the embodiments of an endoscopic instrument which is disclosed here, however they can also be advantageously applied independently of one another without the other aspects.

The invention is hereinafter explained in more detail by way of embodiment examples which are represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 4a, 4b are schematic cross-sectional views of a distal end section of a working channel of an exemplary embodiment of an endoscopic instrument which is disclosed herein;

FIG. 5 is a cross-sectional view of a proximal connection section of an exemplary embodiment of an endoscopic instrument which is disclosed herein;

DESCRIPTION OF PREFERRED EMBODIMENTS

Figures 1, 2A:
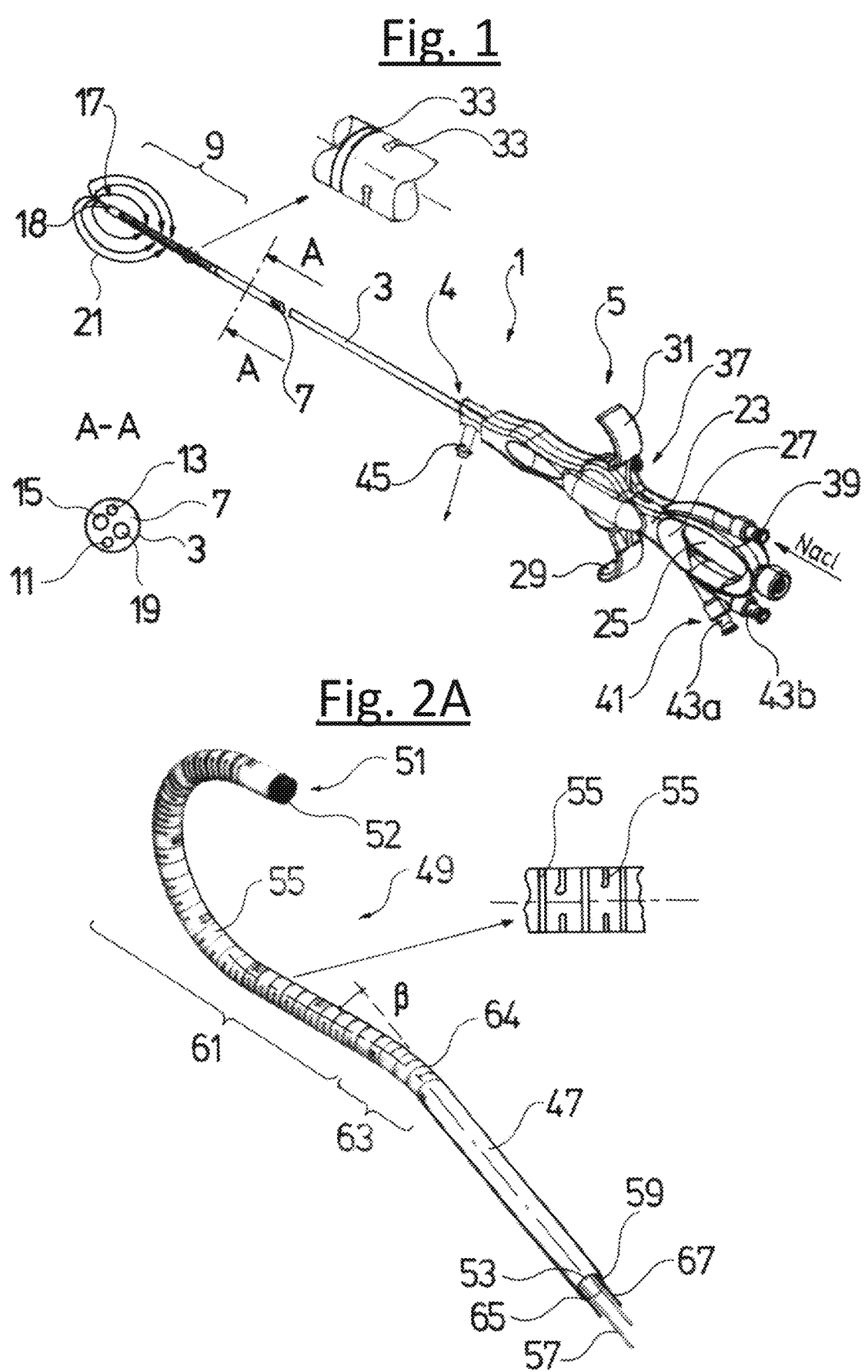
FIG. 1 is a perspective view of an example of an embodiment of an endoscopic instrument which is disclosed herein.
FIG. 2a, 2b are perspective views of a distal end section of an exemplary embodiment of an endoscopic instrument which is disclosed herein.

Referring to the drawings, FIG. 1 by way of example shows an endoscopic instrument 1 which comprises a tubular shank 3 for insertion into a body cavity. The shank 3 is connected to a handling device 5 at a proximal end 4 and in its inner lumen forms a fluid channel 7. The shank 3 furthermore at a distal, bendable shank section 9 is configured in at least partly flexible manner, in order when necessary to be bent by way of the action of the handling device 5.

It is evident in a part-section A-A through the shank 7 that by way of example a first optical and/or electrical lead 11 for the illumination at the distal shank end 17, a second optical and/or electrical lead 13 for taking pictures at the distal shank end 17, a first working channel 15 and a second working channel 19 run in the fluid channel 7. An LED as a light source can be arranged at the distal end of the first lead 11, wherein the lead 11 serves as an electrical electricity supply lead to the LED. Alternatively or additionally, a fiber optic outcoupling as a light source can be arranged at the distal end of the first lead 11, wherein the lead 11 serves as an optical fiber optic. Analogously to this, an objective with a picture senor for taking pictures can be arranged at the distal end of the second lead 13, wherein the lead 11 serves as an electrical electricity supply lead of the picture sensor and for signal transmission. Alternatively or additionally, a fiber optic incoupling can be arranged at the distal end of the second lead 13, wherein the lead 13 serves as an optical fiber optic.

The first working channel 15 preferably has at least double the cross section of the second working channel 19. The first working channel 15 can selectively serve as an insert channel for a shank tool, for example a capture basket, a scissors or a forceps. Alternatively or additionally, even given an inserted shank tool, the first working channel 15 can serve as a feed or discharge conduit of rinsing fluid. The second working channel 19 can preferably serve as an insert channel for a laser fiber optic, in order to be able to destroy kidney stones or urinary stones with laser light. The inner diameter of the second, smaller working channel 19, at least in the bendable shank section 9 should exceed the outer diameter of the laser fiber optic by 30% at the most, in order to ensure a secure leading-through of the laser fibber optic.

All leads 11, 13, 15 and 19 are individually surrounded by the fluid channel 7 in a direct manner. The particularity of this arrangement lies in the fact that the four exemplary leads 11, 13, 15 and 19 are individually arranged in the fluid channel 7 and, if fluid flows there, are consequent peripherally rinsed by the fluid in a direct manner. The complete remaining cross-sectional area of the fluid channel 7 can consequently be used for a fluid. The cross-sectional area of the fluid channel 7 consequently corresponds to the cross-sectional area of a shank interior which is formed by the shank 3 minus the sum of cross-sectional areas of all leads 11, 13, 5, and 19 which run through the shank interior as well as of all further leads which are to be considered. A separate fluid channel which always demands an independent sheathing within the shank 3 is not necessary, since the first working channel 15 can itself be used as a feed or discharge conduit for rinsing fluid even in the case of an inserted shank tool. The shank 3 can consequently be provided with a particularly small outer diameter. With this construction, the possible problem of a more difficult cleaning ability or sterilization ability can be solved by way of the complete endoscopic instrument 1 preferably being configured as a disposable article for disposal after single use, thus does not need to be sterilized at all after use.

Of course, other, less or more leads which can run in the fluid channel 7 in this manner are also conceivable. For instance, leads for transmitting electrical signals and/or electrical power are conceivable. Furthermore, distally arranged light diodes can be provided with electrical power via these, or picture signals can be transmitted from a distally arranged picture sensor. The leads 11, 13, 15 and 19 as well as all alternative or additional leads can each comprise an individual encasing. This can be important particularly in the case of electrical leads, in order to insulate these. Additionally, mechanical leads in the form of control cables can be led in the shank, in order to jointlessly bend the bendable shank section 9 or to control it in is shape in another manner. The mechanical leads for instance can be pull cables or pull wires which are led on lateral inner surfaces in the shank 3.

The distal bendable shank section 9 as a distal region is provided with several slots 33 which give the bendable shank section 9 its movability. The distal bendable shank section 9 is consequently flexible or at least partly flexible, thus semi-flexible. Instead of the use of individual links which are connected to one another in an articulated manner, the shank section 9 can be rendered flexible about at least one axis of curvature by way of a targeted slotting. For this, the slots are preferably incorporated into the shank in the circumferential direction, extend over the complete material thickness of the shank jacket and run over more than half the circumference, for example up to 270°. Two lamella-like parts of the shank 3 which are consecutive along the extension direction of the shank 3 and between which a slot 33 is located in a peripheral surface 35 of the shank 3 are consequently connected to one another by a web which in this case extends in the circumferential direction by way of example by at least 90°. On account of the single-piece configuration, the webs which remain between the individual lamella-like parts always have the tendency to assume an initial, unloaded position, in which the shank 3 preferably runs in a straight line. If the preferably metallic shank 3 is consequently bent by way of a pull cable due to the action of a tensile force, the distal bendable shank section 9 can be jointlessly bent by up to 300°. After the release of the pulling force, by way of the webs which spring back, the shank 3 strives to return back into its straight shape. In order to achieve a uniform flexibility, the slots 33 are arranged axially to one another in a manner such that they lie alternately on a first lateral side of the shank 3 and on a second lateral side of the shank 3 which is diametrical opposite to the first side.

The slots 33 can be incorporated into the shank by way of a machining device which preferably uses a laser. By way of this, a rapid, inexpensive machining can be effected, and such is no obstacle to a configuration of the instrument 1 as a disposable article. Very delicate structures can be created by way of a suitable leading of the beam of the laser. The clear width of the slots 33 can be dimensioned so small, that tissue does not penetrate into the slots 33 and an unhindered displacement of the shank 3 into the operation region can be effected. The slots 33 can be rounded in their profile. Optionally, a coating of the shank 3 can be effected with a lubricative coating. The slotted, bendable shank section 9 is preferably surrounded by a protective tube 199 (see FIG. 7*f*). The protective tube can for example be fabric-reinforced and/or shrunk on. The protective tube can comprise for example bio-compatible plastic.

The fluid channel 7 in the inner lumen of the shank 3 can serve as a feed channel and/or discharge channel for a rinsing fluid which is delivered through the free residual cross section. It is conceivable for rinsing fluid to be fed distally out of the slots which then act as distal fluid channel openings or for rinsing fluid with an annoying tissue suspension to be led away proximally, in accordance with requirements for improving the view at the distal end 17. Given the subsequent use of the fluid channel 7 without the first working channel 15 as a feed channel and/or discharge channel, it is conceivable to temporarily either only feed rinsing fluid or only discharge it. The feeding of the rinsing fluid can be effected for example actively by way of an external pump or passively by way of the hydraulic pressure from a drip which is connected and suspended at a higher level. The discharging can be effected by way of an overpressure in the operation region being generated by the rinsing, by way of which overpressure rinsing fluid can subsequently exit proximally at the outer side along the shank 3. The first working channel 15 however preferably serves as a feed channel and the fluid channel 7 as a discharge channel, or vice versa. By way of this, an undesired fluid flow at the outside on the shank 3 can be largely reduced or completely avoided.

Hence for the continuous rinsing, it can make sense to use the first working channel 15 which extends distally through the fluid channel 7 and which comprises a first distal working channel opening 18 as a feed and/or discharge channel. The cross section of the first distal working channel opening 18 can be smaller than the cross section of the first working channel 15, so that the blocking of the first working channel 15 by tissue which enters via the distal working channel opening 18 is prevented. Alternatively or additionally to this, the cross section of the first working channel 15 can taper towards the distal working channel opening 18. The first working channel 19 can be continuously supplied with rinsing fluid by way of an external pump or one which is arranged in the handing device 5 or from a connected drip which is suspended at a higher level, said rinsing fluid being led distally and exiting directly at the distal shank end 17. The first working channel 15 is consequently a feed channel. On account of the overpressure which sets in, the rinsing fluid gets through the slots 33 and/or lateral rinsing openings 203 (see FIG. 7*b,c*) into the fluid channel 7 and flows proximally back from there. This is indicated in FIG. 1 by the flow lines 21 which lead from a purely axial, distally directed outflow from the distal shank end 17 to a lateral inflow through the slots 33 and/or lateral rinsing openings. The flow direction in the first working channel 15 is consequently in opposite directions to that of the fluid channel 7. Of course, this could also be effected in a reverse constellation by way of rinsing fluid exiting out of the slots 33 and/or the lateral rinsing openings in the distal bendable shank section 9 and being led back at the distal shank end 17 via the first working channel 15. If the slots 33 are surrounded by a protective tube 199 and/or a lubricative coating, then the leading of the fluid can be effected exclusively via lateral rinsing openings 203.

The handling device 5 is merely represent by way of example in FIG. 1. Further handling devices are shown in the FIGS. 6*a-c* ff. All variants of handling devices can be combined with the advantageous configurations of the shank 3 which are outlined here. Furthermore, other handling devices which in their shape differ from the variants which are shown here are also conceivable.

Concerning the handling device 5 in FIG. 1, a housing 23 is shown, said housing by way of example having a grip opening 25 for leading through a thumb and being configured such that the ball of the thumb of a hand then lies on a contact surface 27 which is directed to the shank 3. Two operating levers or triggers 29, 31 which are arranged on lateral sides of the housing 23 which are opposite one another connect directly in grip reach of the other finger of the hand. If the ball of the thumb is located on the contact surface 27 then for instance the lower trigger 29 can be operated by a middle finger whilst the index finger lies on the upper trigger 21. By way of pulling the triggers 29 and 31 to the grip opening 25, the pull cables 11 and 13 which are coupled thereto are pulled. In order to avoid stresses within the shank 3 and to carry out a harmonic movement of the distal bendable shank section 9, the two pull cables could each be configured as a section of an individual pull cable which runs between the two triggers 29, 31 via a guide roller. If therefore for instance the lower trigger 29 is moved, then for example the first pull cable 11 is pulled, wherein the upper trigger 31 is moved in the opposite direction and herein relaxes the second pull cable 13. For this, both triggers 29, 31 could be connected to one another via the guide roller which is not shown here or be coupled to one another in an indirect manner so that they automatically move in opposite directions on actuation.

The first, larger working channel 15 can run on a side 37 of the handling device 5 which faces the upper trigger 31, so that a first proximal working channel opening 39 for the selective introduction of a rinsing fluid, for example NaCl solution or of a shank tool is present there. Other leads, for example the second, smaller working channel 19 for a laser fiber optic can run out into a respective second proximal working channel opening 43*a* or 43*b* at a side 41 which faces the lower trigger 20. The fluid channel 7 comprises a proximal fluid channel opening 45 in the form of a pipe stub which runs transversely to the shank 3 and out of which the rinsing fluid which flows back then finally exits.

Figures 2B, 3A:
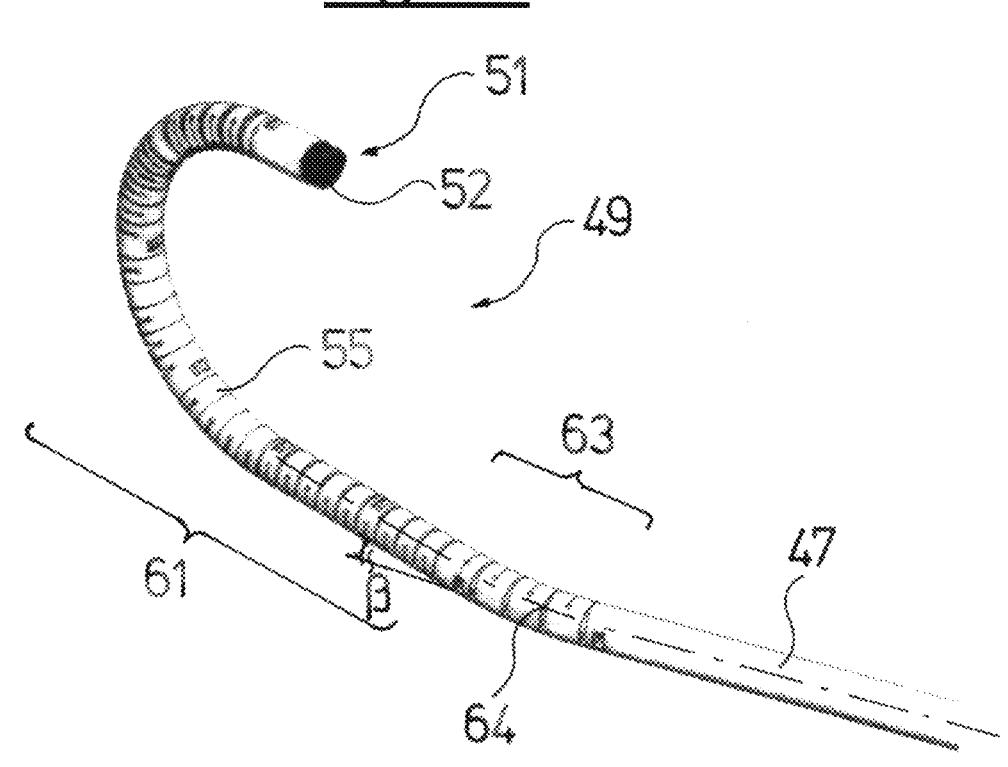
FIG. 3a, 3b, 3c are exploded perspective views of parts of an exemplary embodiment of a working channel of an endoscopic instrument which is disclosed herein.
Figures 6A, 6B, 6C:
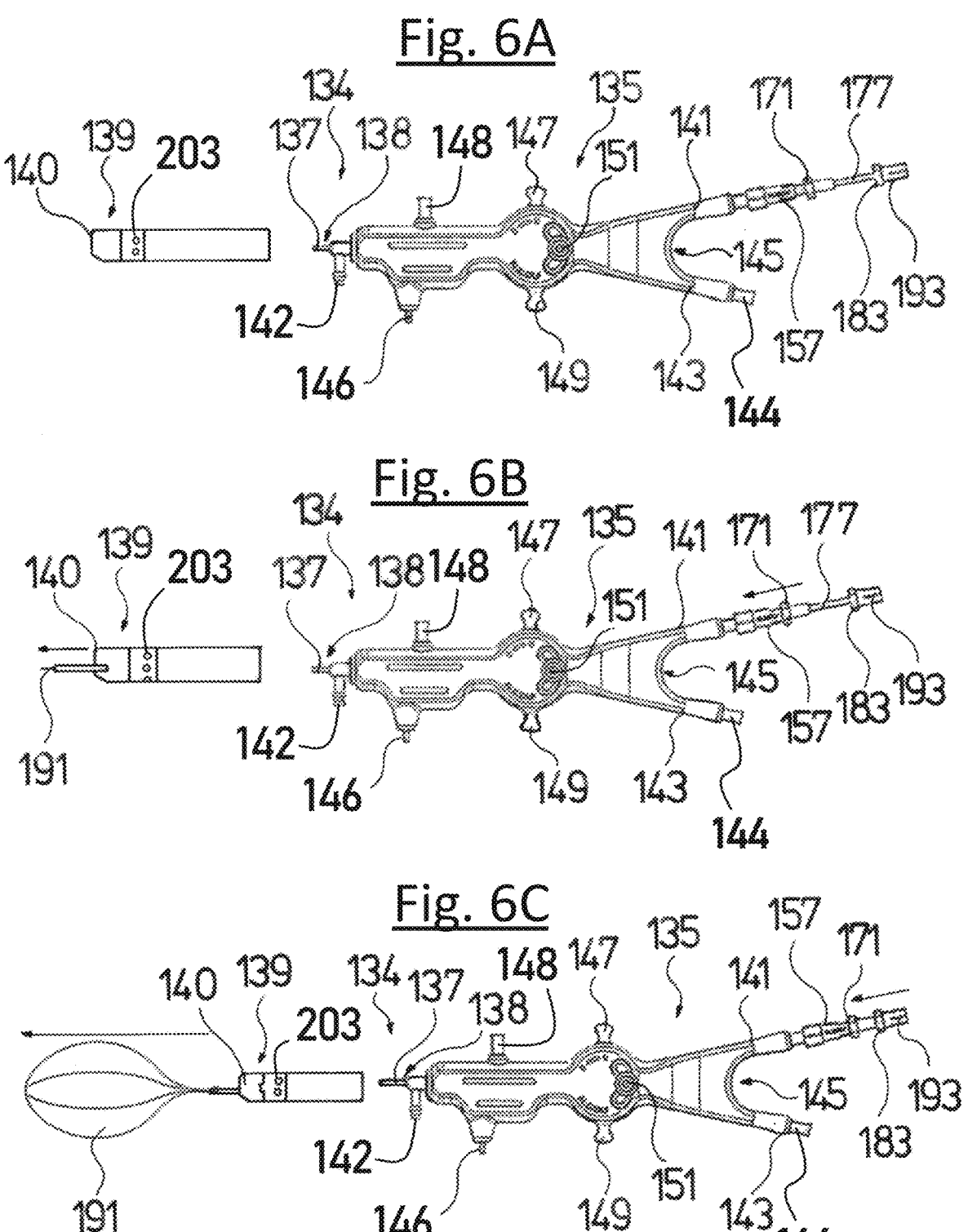
FIG. 6a, 6b, 6c are lateral views of a handling device with detailed views of the distal shank end of an exemplary embodiment of an instrument which is disclosed herein.

A shank 47 of an endoscopic instrument is shown in a part view in FIGS. 2*a* and 2*b*. The view is concentrated onto a flexible distal bendable shank section 49 with a distal end 51 of the shank 3, on which a first distal working channel opening 52 is arranged. The cross section of this first distal working channel opening 52 can be smaller than that of the first working channel 15 which is not shown here. Alternatively or additionally to this, the cross section of the first working channel 15 can taper to the first distal working channel opening 52. The shank 47 proximally comprises a rigid, tubular section which is not visible here and which is connectable to a handling device 5. This can correspond to the handling device 5 of FIG. 1 or be configured as a handling device which is represented in FIG. 6*a-c*.

A fluid channel 53 which is formed in the shank 47 can be recognized with a distal viewing direction. The distal, bendable shank section 49 is configured such that it can be bent in the simplest manner without necessitating dedicated joints which project into the fluid channel 53 or lead to an enlarged outer diameter of the shank 47. For this, the distal, bendable shank section 49 as a distal region is provided with several first slots 55 which run parallel to one another, are distanced to one another and locally completely penetrate the material of the shank 47. The first slots 55 by way of example extend over an angle of 270° in the circumferential direction and herein run around a main extension direction of the shank 47 which runs from a proximal end to the distal end 51. By way of example, slots 55 which are adjacent which is to say are consecutive are offset to one another in the circumferential direction by 180°. The first slots 55 are accordingly arranged axially to one another in a manner such that they alternately lie on a first lateral side of the shank 47 and on a second lateral side of the shank 47 which lies diametrically opposite the first side. As a result, the distal bendable shank section 49 has a very flexible shape. Individual lamella-like parts of the shank 47 which are separated from one another by way of slots 55 can change in their alignment to one another by way of widening or compressing the slots 55. By way of this, the bendable shank section 49 undergoes a jointless bending of up to 300°. This movement of the bendable shanks section 49 can be influenced by mechanical pulls wires 57 and 59 which run in the fluid channel 53. Herewith, a pulling and relaxing of lateral sections of the bendable shank section 40 can be effected in a targeted manner.

The complete shank 47 can be configured in a single-part manner by way of this advantageous configuration, which has a positive effect on the achievable minimal outer diameter of the shank 47. As in the representation of FIG. 1, here too there are two lamella-like parts which are consecutive along the direction of extension of the shank 47 and between which a slot 55 is located, and are consequently connected to one another by a web which in this case extends over 270° in the circumferential direction. On account of the single-piece configuration, the webs which remains between the individual parts tend to assume an initial unloaded position, in which the shank 47 preferably runs in a straight line. If the shank 49 is subsequently bent by way of the action of a tensile force by one of the mechanical leads 57 or 59, the shank 47 after releasing the tensile force has a tendency to return into its straight shape by way of the webs which spring back. The bendable shank section 49 therefore acts like a spring. A protective tube which surrounds the bendable sank section 49 can assist this spring effect which forces it into the initial straight shape.

On account of this arrangement of the first slots 55, a bending can be carried out on a single plane which is spanned by the peripheral side middle points of the slots 55. Concerning the special application in the field of the destruction of kidney stones, the distal bendable shank section 49 is jointlessly bendable by up to 300° on account of the required ability of the stones in the lower caliceal group of the kidneys to be reached.

It is advantageous to be able to also laterally bend the bendable shank section 49 in two opposite directions for example by up to 20 or 25, in order to enlarge the spatial region, in which in particular one can machine the respective stone or another object with a laser. This is achieved by way of subdividing the distal bendable shank section 49 into a first region 61 and into a second region 63, in which differently aligned slots 55 are arranged. In the first region 61 which extends up to the distal end 51, the first slots 55 are each offset to one another by 180°. By way of this, as described above, one realizes a main bending plane. Two slots 64 which in the circumferential direction are offset to the first slots by 90° in the first region are provided in the second region 63 which extends proximally from the first region 61. The second region 63 extends over a significantly shorter stretch that the first region 61, wherein the distances of the slots 55 and 64 in both regions 61 and 63 are preferably identical. The second slots 64 are arranged axially to one another in a manner such that they lie alternately on sides of the shank 47 which are diametrically opposite one another. As a result, on account of the second region 63 which is configured in such a manner, a limited movability in a plane which runs perpendicularly to the main bending plane is possible. The movability can be limited by way of the number of the second slots 64, for example to an angle range of about +/−20. A movement can be realized by two further mechanical leads 65 and 67 which are coupled to the shank 47 distally in front of the second region 63 in a direct manner and can likewise be configured as pull wires. It is by way of the combination of these two bends that it is rendered possible for a laser fiber to exactly scan a recognized object in a relatively large working region.

In FIG. 2a, a slight offset to the left in the plane of the drawing is achieved, as is indicated by the angle β. Here, consequently the first region 61 and herewith the main bending plane is pivoted to a side by about 20. In FIG. 2b, a pivoting in the other direction is shown, as is indicated by the angle β. The distal end 51 of the shank 47 can be moved in a significantly improved manner due to the second region 63 with the slots 55 which are arranged therein as well as due to the additional mechanical leads 65 and 67. On account of the single-piece configuration, one can simultaneously further succeed in the shank 47 having an adequate strength, in order to move the distal end 51 in a direct manner by way of rotating the shank 47.

Figure 3B:
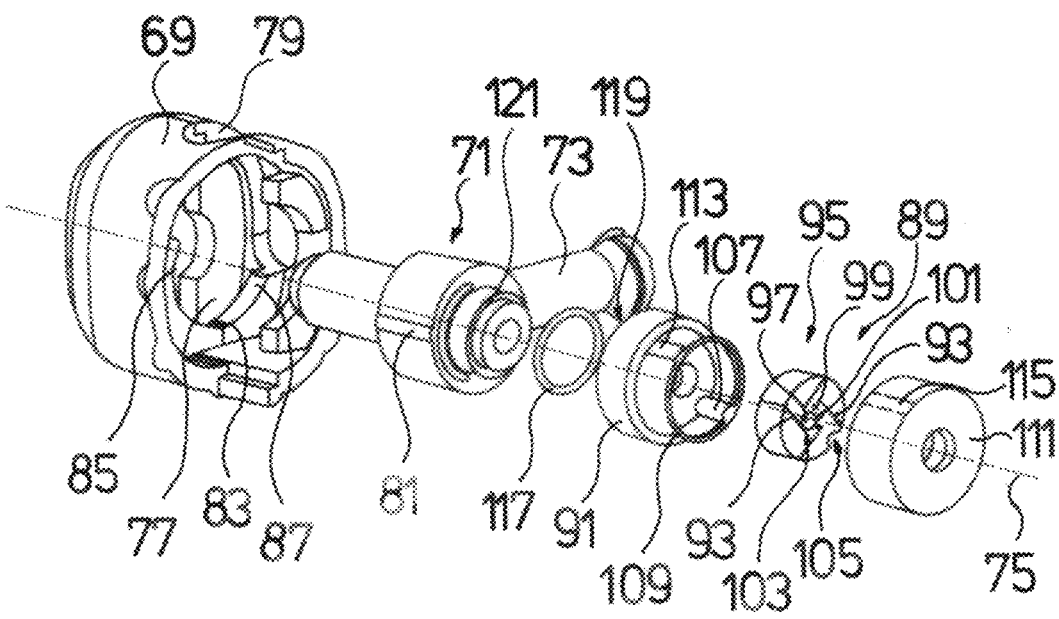
Figure 3C:
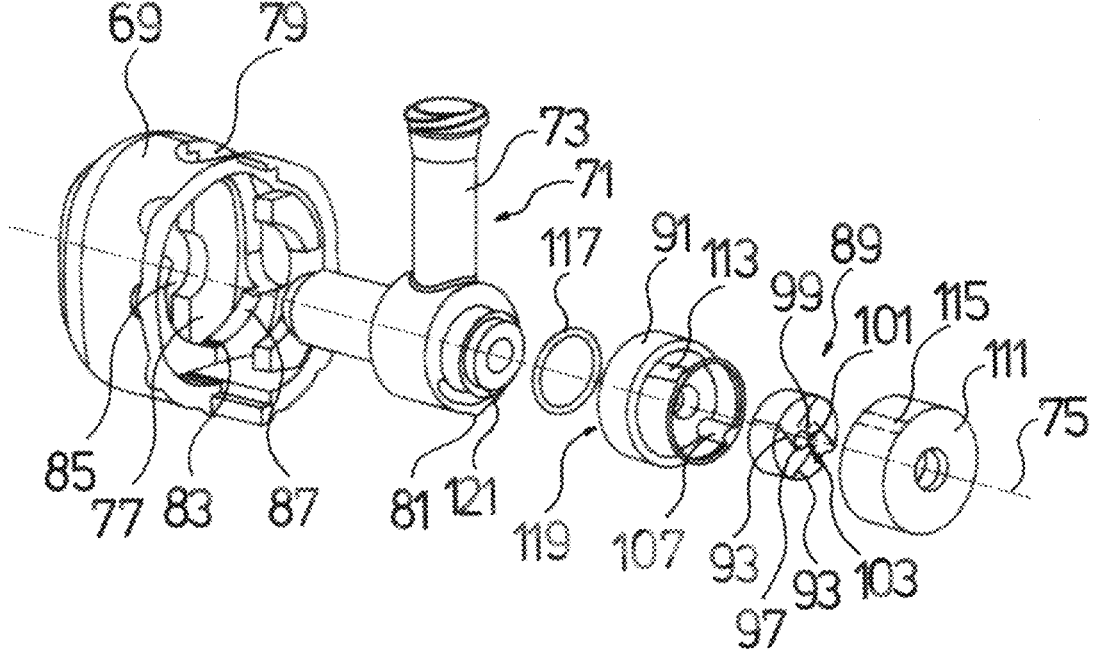

FIGS. 3a to 3c show a detail of an endoscopic device which comprises a fluid channel which as in the preceding figures can be configured as a fluid channel 7 or fluid channel 53. However, only a small part of the device is represented in the figures, so that a shank and a fluid channel are not visible. A part of a control housing 69 is shown, into which control housing a shank connection part 71, with which a shank can be coupled is integrated. This shank is not represented here and can be configured according to the principles of FIGS. 1, 2a, and 2b. However, it can also lend itself to couple a conventional shank to the shank connection part 71, as long as it comprises an aforementioned fluid channel.

A proximal fluid channel opening in the form of a connection pipe stub 73 is arranged on the shank connection part 71, said stub extending outwards transversely to a shank connection axis 75 on an outer periphery. Rinsing fluid which comes from the fluid channel 7, 53 can exit via the connection pipe stub 73. The shank connection part 71 is configured for the integration into a cavity 77 of the control housing 69. A lateral opening 79, through which the connection pipe stub 73 extends outwards connects onto the cavity 77. A radial projection 81 which can latch into correspondingly shaped latching openings 83 and 85 of a radial contour 87 of the cavity 77 is shaped out on a side of the shank connection part 71 which by way of example lies opposite the connection pipe stub 73. The latching openings 83 and 85 by way of example are offset to one another by 90° in a manner in which they run around the shank connection axis 75. As a result, the shank connection part 71 can latch in two rotation positions which are distanced to one another by for example 90°. The lateral opening 79 can be shaped out in a manner corresponding to this.

The shank (not shown) is coupled to the shank connection part 71 in a rotationally fixed manner so that the shank is also rotated by way of rotating the shank connection part 71. By way of this, the direction of the bending of the distal bendable shank section can be influenced. Since on using a fluid channel 7, 53 which is merely defined by a shank jacket, several leads must be led outwards through the control housing 69 without connecting the inner lumen of the fluid channel 7, 53 to the inner lumen of the control housing 69, a sealing means in the form of a seal device 89 is provided. This is shaped in a disc-like manner and is insertable into a seal receiver 91 which in turn is fixedly connected to the shank connection part 71.

The seal device 89 comprises four feed-throughs in the form of slots 93 for leading through mechanical leads, for example pull wires. In this example precisely four slots 93 are shown, so that a shank according to the FIGS. 2a and 2b can also be coupled to this seal device 89. If another shank is to be used, then of course another number of slots 93 can be realized. The shown slots 93 are based for example on radial lines which are shifted in parallel and which are offset to one another by 90° on a circular surface which is covered by the seal device 89. The slots 93 pass through a peripheral surface 95 of the seal device 89 and by way of example project beyond a middle line which runs perpendicularly to the respective slot 93 and intersects a middle point of the seal device. If the pull wires are configured as flat wires, then these can each run through a slot 93 between the shank and the control housing 69 and are hereby gently embraced by the material of the seal device 89.

In order to minimize a friction of the pull wires as much as possible, the seal device 89 is preferably manufactured of a closed-celled foam material. The dimensions of the seal device 89 in the non-inserted state is preferably somewhat larger than the dimensions of the seal receiver 91, so that the seal device 89 needs to be compressed somewhat on insertion and constantly pushes into a relaxed, expanded posture. Hereby, all elements which are led through are sealingly embraced.

The seal device 89 further comprises further recesses 97, 99, 101 and 103 which in accordance with the leads 11, 13, 15 and 19 can have different dimensions. The seal device 89 has a largest recess 97 which belongs to the first working channel 15 which can extend along the extension axis 75 through the control housing 69 to the first proximal working channel opening 39. Three further feed-throughs 99, 101 and 103 in the form of recesses which serve for leading through the leads 11, 13 and the smaller second working channel 19 are arranged adjacently to the largest recess 97. The feed-though 103 which by way of example has the smallest dimensions is suitable for instance for leading through the smaller second working channel 19 with a dimension of significantly below 1 mm, for example 55 mm or less. The two other feed-throughs 99 and 101 belong to the electrical leads 11, 13 which are connected to the distal-side LED or to the picture sensor. The dimensions of the recesses 97, 99, 101, 103 are each somewhat smaller than the cross section of the associated led-through lead 11, 13, 15, and 19, in order to achieve a sealing effect on the lead 11, 13, 15 and 19 at the outside. The seal device 89 is preferably an elastic cell foam block of ethylene-propylene-diene monomer (EPDM), so that the recesses 97, 99, 101 and 103 on leading through the leads 11, 13, 15 and 19 accordingly expand and embrace these in a sealing manner.

The seal device 89 comprises a radial deepening 105 which in a manner corresponding to a radial projection 107 is formed in a sleeve-like section 109 of the sealing receiver 91. By way of this, the rotary position of the seal device 89 is always fixed, so that the seal device 89 follows the rotation on rotating the shank connection part 71.

It is usefully to arrange guide means for guiding the pull wires in the seal receiver 91 and a cover 111 which is fastened thereto, so that the slots 93 of the seal device 89 are always flush with the pull wires on rotating the shank connection part 71. The seal device 89 is therefore loaded exclusively by an axial force of the pull wires. In order to further achieve an ideal guiding of the pull wires, the cover 11 is arranged on the seal receiver 91 in a rotationally fixed manner. For this, a radially outer-lying tongue 113 which is aligned with a radially inner-lying deepening 115 of the cover 111 can be provided on the sleeve-like section 109.

As is represented in FIG. 3b, an additional sealing ring 117 which seals the seal receiver 91 on the shank connection part 71 can be provided. For this, the seal receiver 91 on a deepening 119 which is arranged opposite to the sleeve-like section 109 comprises a sealing surface which can be brought to abut with the sealing ring 117 and an annular surface 121 of the shank connection part 71. The rinsing fluid which flows into the shank connection part 71 via the rinsing channel cannot proximally pass the seal device 89 and flows away radially via the connection pipe stub 73.

A further aspect of the endoscopic instrument is shown in FIGS. 4a and 4b. A fiber optic 123 which in particular is a laser fiber optic in the form of an individual fiber and has an exemplary diameter of 0.45 mm is represented in FIG. 4a. This diameter can preferably include a protective layer of the fiber optic 123, wherein the light-leading core diameter can be for example only 0.272 mm. Of course, the fiber optic 123 can also have an even smaller or a somewhat larger diameter. The fiber optic 123 comprises a light exit end 125 which for optimal radiation characteristics runs in a sharp-edged as possible manner and perpendicularly to the exten-sion axis of the fiber optic 123. However, the pushing of such a fiber optic 123 through a working channel 127 which for instance has a diameter of 1.2 mm or more entails difficulties. The sharp-edged light exit end 125 could jam with the inner wall 129 of the working channel 127 on being pushed through this and could prevent the pushing-through or the fiber optic could 123 even kink. Furthermore, the wall 129 could also be destroyed on jamming if the light exit end 125 bores into the inner wall 129.

In order to prevent this, as is represented in FIG. 4b, an alternative working channel 131 as a second, smaller work-ing channel 19 is provided for the fiber optic 123, and this at least in a bendable section has an inner diameter of only a little more than the diameter of the fiber optic 123 (here 0.45 mm) and by way of example is 0.55 mm. The fiber optic 123 at its light exit end 125 only experiences a very small angle of engagement to an inner wall 133 of the working channel 133, so that a jamming is reliably prevented.

The mentioned diameters in the bendable section are merely to be understood as example. The inner diameter of the working channel 131 for leading through the fiber optic 123, at least in the bendable section should have an inner diameter which does not exceed the outer diameter of the fiber optic 123 by too much. The difference between the two diameters in the bendable section should not be too large since otherwise there is the danger of jamming and/or damage of the working channel 131. It has been found that a diameter difference in the bendable section of maximally 30% can prevent the damaging of the working channel 131.

The inner diameter of the working channel 131 should therefore exceed the outer diameter of the fiber optic 123 at the most by 30% at least in the bendable section, which is the case with the mentioned exemplary diameters.

A further aspect for realizing an endoscopic instrument 134 is shown in FIGS. 5 to 6c. FIGS. 6a to 6c show a handling device 135, onto which a proximal end 138 of a shank 137 is connected. This comprises a distal end 139 which in the plane of the drawing at the left is represented in a somewhat enlarged manner and by way of example comprises a first distal working channel opening 140. A proximal fluid channel opening 142 as well as an electrical connecting cable 146 is arranged on a side which is at the bottom in the plane of the drawing, wherein a rinsing fluid or the like can exit out of the proximal fluid channel opening 142. Here, a separate fluid inlet 148, through which the first working channel 15 can be rinsed with rinsing fluid is arranged on the upper side. Of course, the shank 137 can likewise comprise a distal bendable shank section which is provided with slots as is represented in the preceding figures. It is generally advantageous to configuration the shank in a jointlessly bendable manner towards the distal end 139.

A first limb 141 and a second limb 143 are provided in a Y-arrangement at a proximal end of the handling device 135, between which limbs a contact surface 145 for applying a ball of the thumb of a hand is provided. By way of example, a second proximal working channel opening 144 is provided on the second limb 143. The alignment of the two limbs 141 and 143 to one another as well as the dimensioning of the contact surface 145 are selected such that on gripping the handling device 135, the ball of the thumb bears on the contact surface 145 in a manner such that the handling device 135 forms a direct extension of a lower arm of the user. The user can consequently very comfortably rotate the handling device 135 exclusively by way of supination and pronation of the lower arm about the longitudinal axis of the shank 137, without having to carry out a more complex arm movement. In particular, this is not the case with conventional pistol-like handling devices.

An upper trigger 147 and a lower trigger 149 follow distally on two sides of the handling device 135 which are opposite one another, said triggers being able to be actuated by two fingers of the hand by way of proximal pulling and each being connected to a distally running pull wire. As in the embodiment example in FIG. 1, the upper trigger 147 and the lower trigger 149 could also be coupled to one another, so that both triggers 147 and 149 execute opposite movements. It is conceivable for a guide roller to be present between the triggers 147 and 149, around which guide roller mentioned pull wires configured as a section of a common pull wire are led. However, a cam disc which is coupled to both triggers 147 and 149 as well as a separate pull wire would also be conceivable. An arresting device 151 could be provided for arresting a momentary position of the guide roller or of the individual pull wires. In the represented case, the arresting device 151 is configured as a knurled screw which for example projects into a cam disc and is clamped onto the outer surface of the handling device 135 by way of tightening.

By way of example, a working channel inlet 153 is located on the first limb 141 according to a further aspect of this disclosure, as part of a Luer lock connection, on which working channel inlet a first closure thread 153 is proximally arranged. A shank tool in the form of a capture basket insert is inserted into the instrument 1 through the working channel inlet 153 and is connected. The capture basket insert comprises a connection element 157 which is connected via a second closure thread 159 which is shaped in a manner corresponding to the first closure thread 155. A first rotatable receiving part 161 which is connected to a tube 163 as a jacket element of the capture basket insert is mounted on the connection element 157 of the capture basket insert. The jacket element 163 of the capture basket insert extends through the first working channel 15 through the shank 3. The first receiving part 161 comprises a first displacing section 165 which is provided with a peripheral-side detent 167. This permits the latching in different positions in an opening contour 169 of the connection element 157. By way of displacing the first receiving part 161 in the distal direction along the first displacing section 165, consequently the tube 163 can be distally displaced in the first working channel 15. A first shoulder 171 in the form of a peripheral collar which has a peripheral knurling 173 is arranged on an end of the first displacing section 165 which is opposite to the connection element 157. By way of this, the first receiving part 161 can be gripped and rotated. The peripheral-side detent 167 is therefore preferably configured in the form of grooves which are arranged parallel to one another and which have a rounded profile cross section. A manual displacing in the distal or proximal direction can lead to the release and the reaching of a latching.

A second receiving part 177 is arranged in an inner lumen 175 of the first receiving part 161. This comprises a second displacing region 179, with which the relative position of the second receiving part 177 to the first receiving part 161 can be adjusted. The second receiving part 177 is simultaneously connected to the first receiving part 161 via a rotationally fixed, displaceable connection. The second receiving part 177 therefore directly follows the movement of the first receiving part 161. The second receiving part 177 is connected to a pull wire 181 which extends through the jacket element of the capture basket insert which is configured as a flexible tube 163. The second receiving part 177 further at an end of the second displacing section 179 which is away from the first receiving part 161 comprises a second shoulder 183 in the form of a peripheral collar which is likewise provided with a knurling 185. A user can consequently easily grip and rotate the receiving parts 161 and 177. On account of the fixed connection between the components, the flexible tube 163 and the pull wire 181 are also rotated. The second receiving part 177 likewise comprises a detent 187 which can latch with an opening contour 189 of the first receiving part 161. The position of the second receiving part 17 can consequently always be set in a fixed manner with respect to the first receiving part 161.

As is represented in the FIGS. 6a to 6c, on account of this configuration a particular advantageous construction of a capture basket 191 can be realized, said capture basket being arranged in the jacket element 163 of the capture basket inert and being protected by this. The capture basket 191 is configured in such an elastic manner that it can be completely retracted into the jacket element 163 and can be pushed out of this by way of a distal movement, where it expands to its full size. A kidney stone or the like can be gripped by way of a targeted movement of the capture basket 191, wherein the gripping is effected by way of a proximal pulling of the pull wire 181 and the capture basket is compressed again by way of this. FIG. 6a shows the first receiving part 161 and the second receiving part 177 in the proximal position. This means that an actuation grip 193 is pulled out of the handling device 135 as far as possible.

As is evident in the enlarged representation of the distal tip 139 of the shank 137, the jacket element 163 of the capture basket insert does not extend beyond the distal shank tip 139. By way of moving the first receiving part 161 over the complete first displacement path 165 in the distal direction, so that the first shoulder 71 lies on the connection device 157 in a flush manner, the flexible tube 163 projects out of the distal shank tip 139 for example by about 5 mm. By way of pushing in the second receiving part 177 in the distal direction, the capture basket 191 can be pushed out of the flexible tube 163, so that it unfolds. 5 mm can be suitable as a displacement path for the flexible tube 163. It is conceivable to provide a significantly greater length, for example 20 mm, for the unfolding of the capture basket 191.

The particular advantage of this arrangement with the distally displaceable jacket element 163 of the capture basket insert and the rotatable connection lies in the fact that the capture basket 191 by way of acting upon the handle 193 can be easily rotated in all unfolding states. Simultaneously, by way of actuating the handle 193, an advancing and unfolding of the capture basket 191 by the hand which indeed does not grip the handling device 135 is permitted. If an object is gripped by the wire capture basket 191, then the object can be firmly held by way of retracting the second receiving part 177. On account of the detent 187, the object remains caught, without it having to be actively firmly held. The capture basket can accordingly be very easily actuated by an individual user, and a second user, with whom one must intensively communicate during the operation, is not necessary.

On account of the second, smaller working channel 19, a laser fiber optic 123 can be led onto the distal shank tip 17 parallel to the capture basket insert in the first working channel 15, in order for example to be able to smash a kidney stone by way of laser light. The second, smaller working channel 19 ends at the proximal side on the second proximal working channel opening 144 on the second limb 143 of the handling device 135.

In FIGS. 7a-f, the shank 3, in particular the bendable shank section 9, 49 of the shank 3 and the distal shank end 17, 51, 139 are shown in more detail. A distal end sleeve 195 is not shown in FIGS. 7a-c, and this is shown in more detail in FIGS. 7d-f. The distal shank end 17, 51, 139 comprises a connection sleeve 197, by way of which the end sleeve 195 is positively fastened to the shaft 3 in a rotationally fixed manner (see FIG. 7f). The end sleeve 195 comprises a recess 199 and the connection sleeve 197 an indentation 201 which is shaped in a manner which correspondingly matches the recess 199, by which means a rotationally fixed positive connection between the end sleeve 195 and the connection sleeve 197 is achieved.

The connection sleeve 197 in an overlapping section overlaps the distal end of the slotted bendable shank section 9, 49. Lateral rinsing openings 203 here in the form of eight radial through-bores which are distributed circumferentially are present in the overlapping section. Since the slots 33, 55, 64 of the bendable shank section 9, 49 are here surrounded by a protective flexible tube 205 (see FIG. 7f, not shown in FIG. 7a-e), the rinsing openings 203 serve as a distal rinsing outlet or rinsing inlet of the fluid channel 7, 53. The thickness of the connection sleeve 197 corresponds roughly to the thickness of the protective sleeve 205, so that the radial outer surfaces of the protective flexible tube 205, connecting sleeve 197 and end sleeve 195 when abutting one another are flush with one another without edges (see FIG. 7f).

Figures 7A, 7B, 7C, 7D, 7E, 7F:
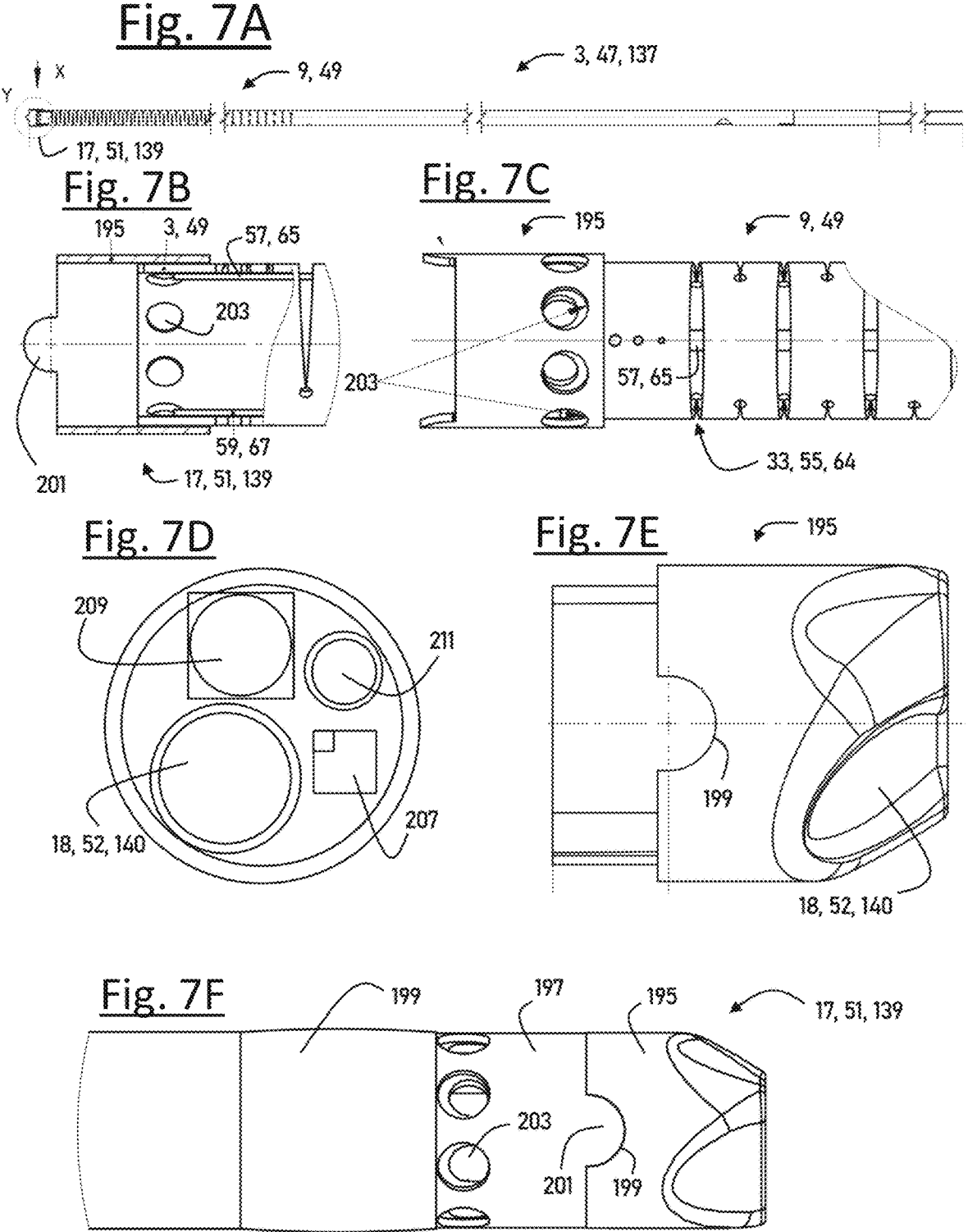
FIG. 7a, 7b, 7c, 7d, 7e, 7f are different views on the shank and in particular the distal shank end of an exemplary embodiment of an endoscopic instrument which is disclosed herein.

The pull wires 57, 59, 65, 67 which in a manner lying diametrically opposite (here: at the top 57, 65 and at the bottom 59, 67) extend through the shank 3 on the shank inner surface in order to be able to bend the bendable shank section 9, 49 jointlessly upwards or downwards are shown in FIG. 7b. For this, the slots 33, 55, 64 are configured in a wedge-like manner, so that the clear width of the slots 33, 55, 64 is largest at the middle where the pull wires 57, 59, 65, 67 run, and taper in the circumferential direction towards the ends. The ends of the slots 33, 55, 64 comprise round recesses, in order, given the bending of the shank material, to reduce the stresses and to reduce material tears or the risk of plastic deformations of the shank material. The jointless bending of the shank section 9, 49 should be effected by way of an elastic as possible deformation of the slotted shank material which has a restoring effect into the straight shank shape.

The arrangement of a light source in the form of an LED 207, an objective 209 with a picture sensor lying therebehind, the first distal working channel opening 18, 52, 140 of the first working channel 15 and a second distal working channel opening 211 of the second working channel 19 in the distal end sleeve 195 are shown in a front elevation in FIG. 7d. The extremely small size conditions are to be noted. The outer diameter of the distal end sleeve 195 can be 3 mm or less. The LED 207 can be 0.55 mm wide and the picture sensor 209 less than 1 mm wide. The first distal working channel opening 18, 52, 140 can have an inner diameter of 1.2 mm or less and the second distal working channel opening 211 an inner diameter of 0.55 mm or less, The distal-side light outcoupling of a laser fiber optic 123, said fiber optic being pushed through the second working channel 19, can be placed on the second distal working channel opening 211. The tool head of a shank tool, for example a capture basket insert or a forceps or scissor instrument, these being able to be pushed through the first working channel 15, can be led out of the first distal working channel opening 18, 52, 140. The first working channel 15 can moreover be used as a feed conduit or discharge conduit of rinsing fluid which is accordingly led away or fed via the lateral rinsing openings 203 and the fluid channel 7, 53. A feed of clear rinsing fluid via the first working channel 15 and a discharge via the lateral rinsing openings 203 and the fluid channel 7, 53 is preferred, in order to obtain a clear distal view.

It is shown in FIG. 7e that the distal end sleeve 195 is beveled at the front side, so that in particular the first distal working channel opening 18, 52, 140 runs at an angle to the longitudinal axis of the shank 3. Preferably, the second distal working channel opening 211 is also beveled (not visible in FIG. 7e). The respective distal openings in the end sleeve 195 for the LED 207 and the objective 209 can also be beveled, in order to improve the respective illumination or the viewing angle. The one or more bevelings of the distal shank tip 17, 51, 139 have the further advantages that the distal shank tip 17, 51, 139 can be led more simply through a ureter or kidney tube or a trocar or catheter.

Figures 8A, 8B, 8C, 8D, 8E:
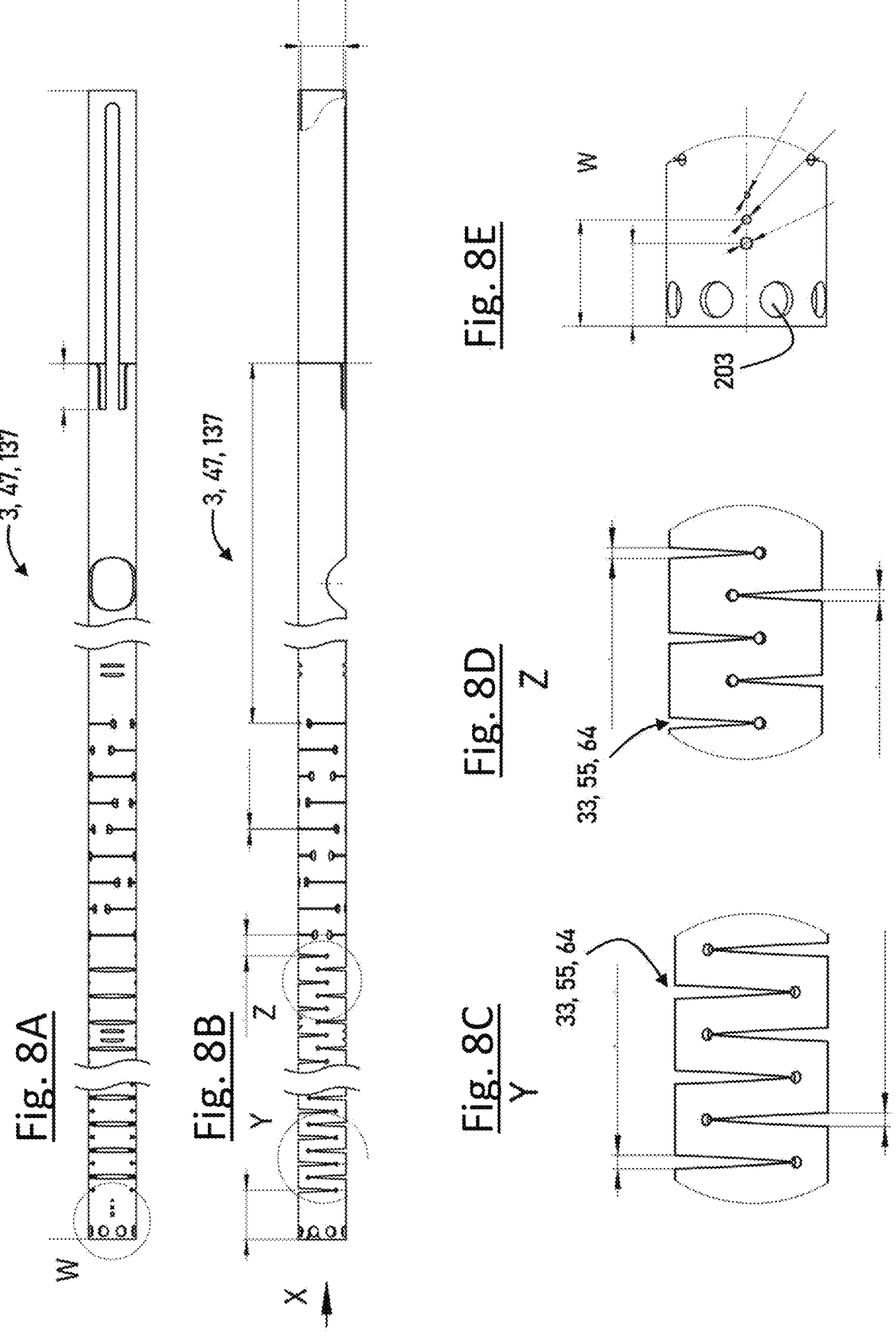
FIG. 8a, 8b, 8c, 8d, 8e are further views on the shank and in particular a bendable shank section of an exemplary embodiment of an endoscopic instrument which is disclosed herein.

FIGS. 8a-e show the single-part metallic tubular main body of the shank 3, 47 which comprises the rinsing openings 203, the slots 33, 55, 64 and the proximal fluid channel opening 45, 73, 142. The bendable shank section 9, 49 with the slots 33, 55, 64 preferably comprises at least two sub-sections Y, Z, wherein the axial distances between the slots 33, 55, 64 are different in the sub-sections X, Z. Preferably, the distances between the slots 33, 55, 64 in a first sub-section Y is smaller than in a second sub-section Z, wherein the first sub-section Y is arranged distally of the second sub-section Z. By way of this, a greater curvature can be achieved in the first sub-section Y than in the second sub-section Z. Furthermore, the first sub-section Y is less flexurally rigid than the sub-section Z, so that the bendable shank section 9, 49 rolls in given bending from the distal tip 17, 51, 139. By way of this, a particularly good mobility of the distal tip 17, 51, 139 and a particularly large bending range of up to 300° can be achieved in a small space. As is shown in FIG. 8c,d shows, the clear width of the slots 33, 55, 64 in the first sub-section Y can be larger than in the second sub-section Z. This can likewise assist the bending ability of the shank section 9, 49 which is improved in the distal direction. The clear width and/or the slot distances can gradually vary within and/or between the sub-sections Y, Z, so that the sub-sections Y, Z can run into one another. The sub-sections Y, Z can be arranged adjacently to one another or separately from one another.

Figures 9A, 9B, 9C, 9D:
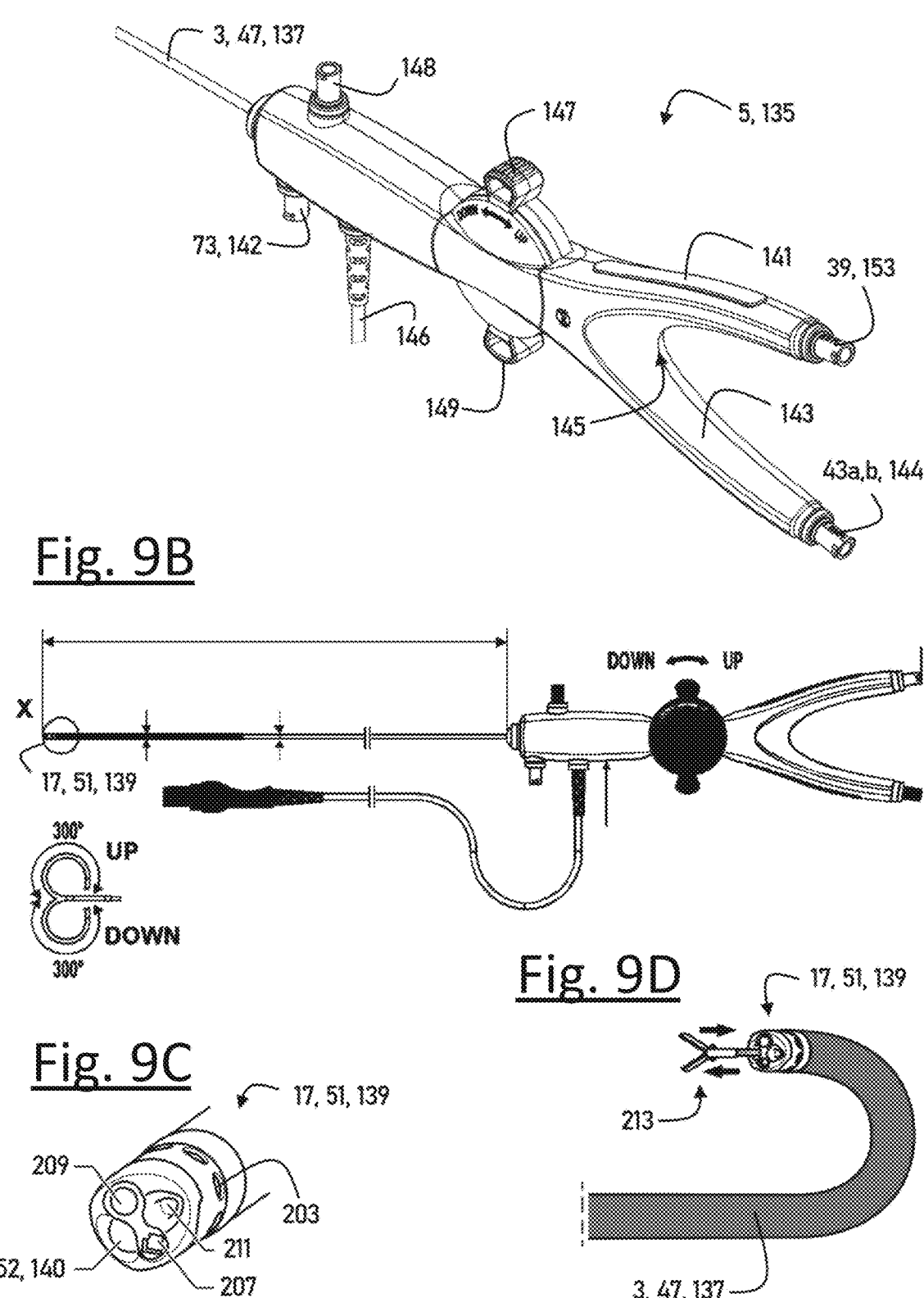
FIG. 9a, 9b, 9c, 9d are different views on an embodiment example of an endoscopic instrument which is disclosed herein.

FIGS. 9a,b show a further configuration of the Y-shaped handling device 5, 135. The instrument which is shown in FIG. 9b can be inexpensively manufactured as a sterilized disposable product which is preassembled on the part of the factory. Once again, it is emphasized how the distal shank tip 17, 51, 139 can be bent upwards or downwards by up to 300° by way of pulling the triggers 147, 149. FIG. 9c shows the distal shank tip 17, 51, 139 in a perspective view with beveled working channel openings 18, 52, 140, 144. FIG. 9d illustrates how a shank tool in the exemplary form of a forceps instrument 213 can be pushed through the first working channel 15 and is axially positionable given a bent shank section 9, 49.

Figures 10A, 10B, 10C:
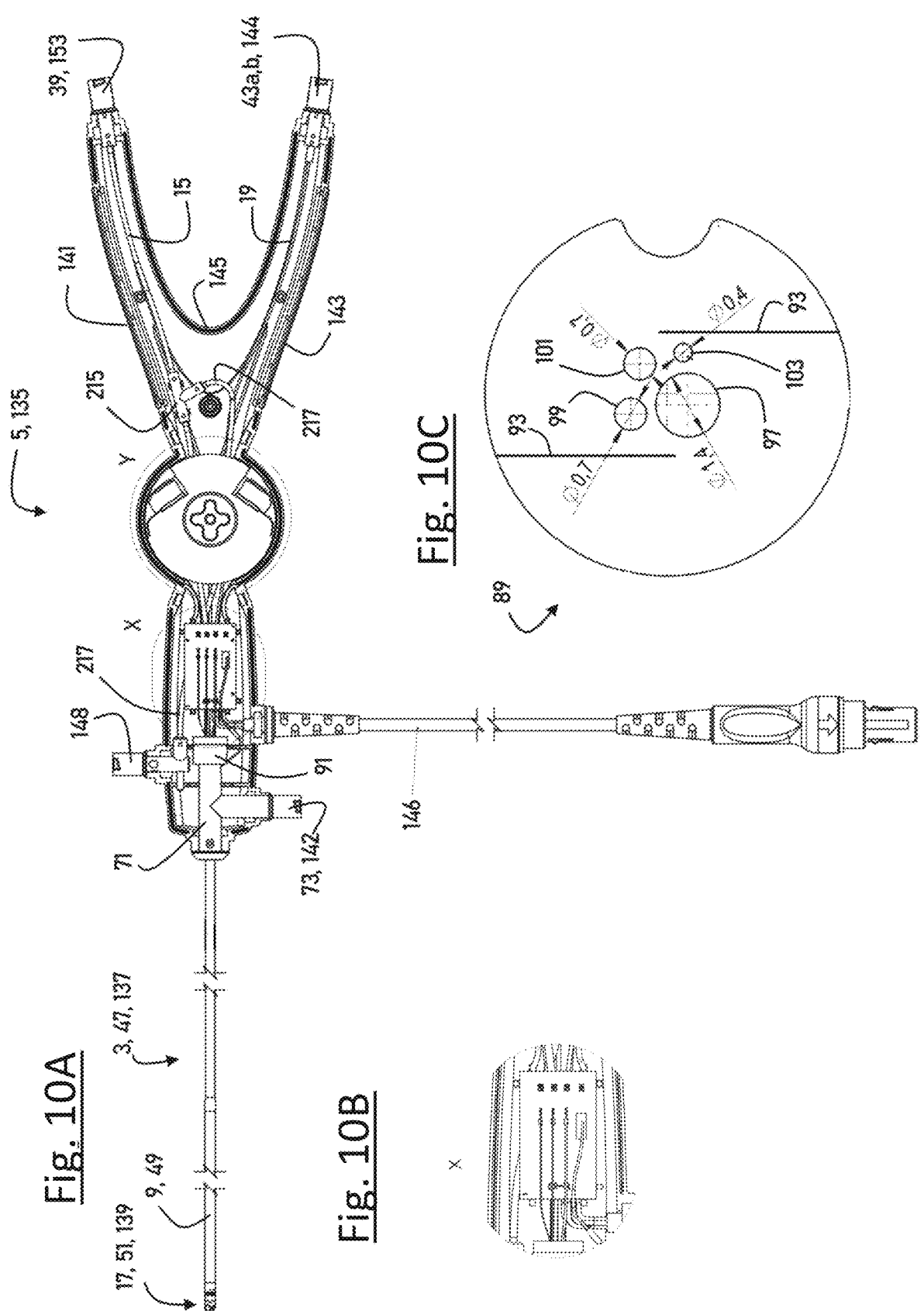
FIG. 10a, 10b, 10c are further views of the embodiment example according to FIG. 9a-d.

In inner workings of the Y-shaped handling device 5, 135 is shown in more detail in a longitudinal section in FIGS. 10a,b. FIG. 10b herein shows an enlarged detail X. FIG. 10c shows an enlarged representation of the seal device 89 in the form of a cell foam block which is seated in the seal receiver 91 and proximally seals the fluid channel 7, 53. The seal device 89 comprises recesses 97, 99, 101 and 103 for leading through the leads 11, 13, 15 and 19 which in accordance with the leads 11, 13, 145 and 19 have different dimensions. The seal device 89 has a largest recess 97 which belongs to the first working channel 15 which can extend along the extension axis 75 through the control housing 69 to the proximal working channel opening 39. Three further feed-throughs 99, 101 and 103 in the form of recesses are arranged adjacently to the largest recess 97 and serve for leading through the leads 11, 13 and the smaller second working channel 19. The feed-through 103 which by way of example has the smallest dimensions, is suitable for instance for leading through the smaller second working channel 19 with a dimension of significantly below 1 mm, for example 0.55 mm or less. The two other feed-throughs 99 and 101 belong to the electrical leads 11, 13 which are connected to the distal-side LED 207 and the picture sensor 209 respectively. The dimensions of the recesses 97, 99, 101 and 103 are each somewhat smaller than the cross section of the associated led-through lead 11, 13, 15 and 19, in order to achieve a sealing effect on the lead 11, 13, 15, and 19 at the outside. The seal device 89 is preferably configured as an elastic cell foam block of ethylene-propylene-diene monomer (EPDM), so that the recesses 97, 99, 101 and 103 accordingly expand on leading through the leads 11, 13, 15 and 19 and embrace these in a sealing manner. The two slots 93 which are arranged offset to one another serve for the sealed leading-through of the two pull cables 57, 59. The radial deepening 105 serves for the rotation lock of the seal device 89.

It is further illustrated in FIG. 10a how the first working channel 15 can be supplied with rinsing fluid via the upper-side fluid inlet 148, so that the first working channel 15 can serve as a feed channel of rinsing fluid. For this, a T-connection piece 215 is arranged in the first working channel 15 within the handling device 5 and is connected to the upper-side fluid inlet 148 via a rinsing conduit 217.

Herewith, a drip which is hung up or a pump can be connected to the fluid inlet 148, so that rinsing fluid runs through the rinsing conduit 217 into the first working channel 15.

It is to be noted that the features of the previously described embodiment examples can be arbitrarily combined with one another.

While specific embodiments of the invention have been shown and described in detail to illustrate the application of the principles of the invention, it will be understood that the invention may be embodied otherwise without departing from such principles.

LIST OF REFERENCE CHARACTERS 1 endoscopic instrument
3 shank
4 proximal end of the shank
5 handling device
7 fluid channel
9 bendable shank section
11 first optical or electrical lead
13 second optical or electrical lead
15 first working channel
17 distal end/distal tip of the shank
18. first distal working channel opening
19 second working channel
21 flow lines/backflow fluid
23 housing
25 grip opening
27 contact surface
29 lower trigger/operating lever
31 upper trigger/operating lever
33 slot
35 peripheral surface
37 upper side of the handling device
39 proximal end
41 lower side of the handling device
43a, 43b second proximal working channel opening
45 proximal fluid channel opening
47 shank
49 bendable shank section
51 distal end of the shank
52 first distal working channel opening
53 fluid channel
55 first slot
57 mechanical lead (pull wire)
59 mechanical lead (pull wire)
61 first region
63 second region
64 second slot
65 mechanical lead (pull wire)
67 mechanical lead (pull wire)
69 control housing
71 shank connection part
73 proximal fluid channel opening/connection pipe stub
75 shank connection axis
77 cavity
79 lateral opening
81 radial projection
83 latching opening
85 latching opening
87 radial contour
89 seal device
91 seal receiver
93 slot/feed-through
95 peripheral surface 97 feed-through
99 feed-through
101 feed-through
103 feed-through
105 radial deepening
107 radial projection
109 sleeve-like section
111 cover
113 radially outer-lying tongue
115 radially inner-lying deepening
117 sealing ring
119 deepening
121 annular surface
123 fiber optic
125 light exit end
127 conventional working channel
129 inner wall
131 working channel
133 inner wall
134 endoscopic instrument
135 handling device
137 shank
138 proximal end of the shank
139 distal end of the shank
140 first distal working channel opening
141 first limb
142 proximal fluid channel opening
143 second limb
144 proximal second working channel opening
145 contact surface
146 electrical connection cable
147 upper trigger/operating lever
148 fluid inlet
149 lower trigger/operating lever
151 arresting device
153 working channel inlet
155 first closure thread
157 connection element
159 second closure thread
161 first receiving part
163 jacket element of the shank tool
165 first displacing section
167 detent
169 opening contour
171 first shoulder/collar
173 knurling
175 inner lumen
177 second receiving part
179 second displacing section
181 pull wire
183 second shoulder/collar
185 knurling
187 detent
189 opening contour
191 capture basket
193 actuation grip
195 end sleeve
197 connection sleeve
199 recess
201 indentation
203 rinsing openings
205 protective sleeve
207 LED
209 objective
211 second distal working channel opening 213 forceps instrument
215 T-Connection piece
217 fluid conduit
β angle (lateral offset)

The invention claimed is:

1. An endoscopic instrument for inserting into a body of a patient, wherein the instrument comprises
    a tubular shank;
    at least two electrical, mechanical and/or optical leads which run through the shank,
wherein a fluid channel is formed in the shank, the at least two electrical, mechanical and/or optical leads comprising at least two pull wires in a form of flat wires for bending a distal end of the shank; and
    a sealing means which forms a proximal end of the fluid channel and comprises feed-throughs for the leads, wherein the sealing means comprises at least two slots as the feed-throughs which pass through a peripheral surface of the sealing means and each slot partly extends through the sealing means, wherein the sealing means has a disc-shaped, round shape, wherein the sealing means is coupled to the shank in a rotationally fixed manner,
wherein the rotationally fixed coupling is realized by positive-fit means which in the sealing means and in a seal receiver are formed in a manner corresponding to one another.

2. An endoscopic instrument according to claim 1, wherein the sealing means comprises an elastomer cell foam block arranged at a proximal end region of the shank and/or in a handling device which is connected or connectable to a proximal end region of the shank.

3. An endoscopic instrument according to claim 2, wherein the cell foam block comprises a closed-celled configuration.

4. An endoscopic instrument according to claim 1, wherein the leads are led through the sealing means through the feed-throughs, wherein the feed-throughs each have an initially smaller diameter than the associated led-through lead, and are elastically widened by way of the led-through lead.

5. An endoscopic instrument according to claim 1, wherein the positive-fit means is realized in the form of a peripheral-side tongue and groove arrangement.

6. An endoscopic instrument according to claim 1, wherein the sealing means comprises four slots as the feed-throughs, said slots being arranged distanced to one another in the sealing means.

7. An endoscopic instrument according to claim 1, wherein the slots are based on radial lines which are displaced in parallel and which are offset to one another by at least 90° on a surface which is covered by the sealing means.

8. An endoscopic instrument according to claim 1, wherein the sealing means is manufactured from a material which comprises polyethylene or a cellular rubber.

9. An endoscopic instrument according to claim 1, further comprising a control housing and a shank connection part rotatably arranged in the control housing and is fixedly or releasably connectable to the shank.

10. An endoscopic instrument according to claim 9, wherein the shank connection part comprises a connection pipe stub which extends radially outwards from a shank connection axis.

11. An endoscopic instrument according to claim 1, wherein the fluid channel individually directly surrounds the at least two leads which run through the shank.

12. An endoscopic instrument according to claim 1, wherein the fluid channel serves as a feed channel and/or discharge channel.

13. An endoscopic instrument according to claim 1, wherein the fluid channel comprises a distal fluid channel opening and a proximal fluid channel opening, wherein the proximal fluid channel opening is arranged laterally on the shank and can be subjected to fluid pressure or a fluid vacuum.

14. An endoscopic instrument according to claim 1, wherein the instrument comprises a handling device, wherein the handling device is fixedly connected or is releasably connectable to a proximal end of the shank.

15. An endoscopic instrument according to claim 1, wherein the shank at least in a bendable shank section is jointlessly bendable by up to 300°.

16. An endoscopic instrument according to claim 1, wherein the instrument or at least the shank is configured as a disposable article for disposal after a single use.

17. An endoscopic instrument according to claim 1, wherein a cross-sectional area of the fluid channel corresponds to a cross-sectional area of a shank interior which is formed by the shank, minus a sum of the cross-sectional areas of all leads which run through the shank interior.

18. An endoscopic instrument according to claim 1, wherein the shank in a distal bendable shank section comprises a plurality of slots.

19. An endoscopic instrument according to claim 18, wherein the slots only extend over a part of the shank periphery in the circumferential direction.

20. An endoscopic instrument according to claim 18, wherein the slots are arranged axially to one another such that the slots alternately lie on a first lateral side of the shank and a second lateral side of the shank which lies diametrically opposite the first.

21. An endoscopic instrument according to claim 18, wherein the slots form a distal fluid channel opening for the fluid channel and locally increased flexibility of the shank for the bending of a distal shank end.

22. An endoscopic instrument according to claim 1, wherein the instrument comprises a working channel which runs through the shank and which is directly surrounded by the fluid channel.

23. An endoscopic instrument according to claim 22, wherein the working channel forms a lead through for leading through a laser fiber optic, a capture basket or a Dormia loop.

24. An endoscopic instrument according to claim 22, wherein the working channel forms a feed and/or discharge channel with a flow direction which runs opposite with respect to the fluid channel.

25. An endoscopic instrument according to claim 22, wherein the working channel runs axially through the sealing means.

26. An endoscopic instrument according to claim 22, wherein the working channel comprises a distal working channel opening and a proximal working channel opening.

27. An endoscopic instrument according to claim 26, wherein the proximal working channel opening is arranged proximally of the proximal end of the fluid channel.

28. An endoscopic instrument according to claim 26, wherein the distal working channel opening is arranged distally of a distal fluid channel opening of the fluid channel.

29. An endoscopic instrument according to claim 26, further comprising a handling device, wherein the handling device is fixedly connected or releasably connectable to a proximal end of the shank, wherein the proximal working channel opening is formed by the handling device.

30. An endoscopic instrument according to claim 26, wherein the cross section of the distal working channel opening is smaller than the cross section of the working channel.

31. An endoscopic instrument according to claim 30, wherein the cross section of the working channel tapers towards the distal working channel opening.

32. An endoscopic instrument according to claim 1, wherein a through-flow direction and/or a through-flow rate through the fluid channel is selectable or can be set.

33. An endoscopic instrument according to claim 1, wherein a distal shank end is jointlessly controllably bendable.

34. An endoscopic instrument for inserting into a body of a patient, wherein the instrument comprises:

a tubular shank;

at least two electrical, mechanical, and/or optical leads which run through the shank, wherein a fluid channel is formed in the shank, and wherein the at least two electrical, mechanical, and/or optical leads comprise at least two flat pull wires configured to bend a distal end of the shank; and a sealing means which forms a proximal end of the fluid channel and comprises feed-throughs for the leads, wherein the sealing means comprises at least two slots passing through a peripheral surface of the sealing means and forming the feed-throughs, each of the two slots partly extending through the sealing means, the sealing means comprising a round disc coupled to the shank with a rotationally fixed coupling comprising a positive-fit formed formed between corresponding surfaces of the round disc and a seal receiver in a manner corresponding to one another.

35. An endoscopic instrument according to claim 34, wherein the sealing means comprises elastic material configured to seal leads of varying dimensions and wherein the feed-throughs provide a sealing effect by adapting to cross-sectional shapes of the leads and channels to allow for operation under varying mechanical and fluidic conditions.

* * * * *